US011179475B2

(12) United States Patent
Hedrick et al.

(10) Patent No.: US 11,179,475 B2

(45) Date of Patent: Nov. 23, 2021

(54) BIODEGRADABLE FUNCTIONAL POLYCARBONATE NANOPARTICLE CARRIES FOR DELIVERING MOLECULAR CARGO

(71) Applicants: International Business Machines Corporation, Armonk, NY (US); Agency for Science, Technology and Research, Singapore (SG)

(72) Inventors: James L. Hedrick, Pleasanton, CA (US); Nathaniel H. Park, San Jose, CA (US); Yi Yan Yang, Singapore (SG); Zhi Xiang Voo, Singapore (SG); Jeremy Tan, Singapore (SG)

(73) Assignees: INTERNATIONAL BUSINESS MACHINES CORPORATION, Armonk, NY (US); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 16/203,024

(22) Filed: Nov. 28, 2018

(65) Prior Publication Data

US 2020/0164088 A1 May 28, 2020

(51) Int. Cl.

| | |
|---|---|
| ***A61K 31/7034*** | (2006.01) |
| ***A61K 31/74*** | (2006.01) |
| ***A61K 8/90*** | (2006.01) |
| ***A61K 8/81*** | (2006.01) |
| ***C08L 69/00*** | (2006.01) |
| ***A61K 47/69*** | (2017.01) |
| ***A61K 47/60*** | (2017.01) |
| ***A61K 47/24*** | (2006.01) |
| ***A61P 25/16*** | (2006.01) |
| ***A61K 9/48*** | (2006.01) |
| ***A61K 9/00*** | (2006.01) |
| ***A61K 31/473*** | (2006.01) |

(52) U.S. Cl.

CPC ........ *A61K 47/6935* (2017.08); *A61K 9/0085* (2013.01); *A61K 9/4833* (2013.01); *A61K 31/473* (2013.01); *A61K 47/24* (2013.01); *A61K 47/60* (2017.08); *A61P 25/16* (2018.01)

(58) Field of Classification Search

CPC .... C08L 69/00; C08L 2203/02; C08L 69/005; C08L 2666/18; A61K 8/8152; A61K 31/69; A61K 47/64; A61K 2800/56; A61K 47/6929; A61K 2039/57; A61K 2039/6093; A61K 31/7034; A61K 6/887; A61K 8/90; C08K 5/55

See application file for complete search history.

(56) References Cited

U.S. PATENT DOCUMENTS

| | | | | |
|---|---|---|---|---|
| 2010/0029545 A1 | 2/2010 | Sumerlin et al. | | |
| 2011/0268807 A1 | 11/2011 | Su et al. | | |
| 2015/0045419 A1 | 2/2015 | Lam et al. | | |
| 2015/0157723 A1* | 6/2015 | Chan | .................... | A61K 31/704 424/489 |
| 2018/0126014 A1 | 5/2018 | Zhou et al. | | |

OTHER PUBLICATIONS

Wang et al. Biocatalytic Fabrication of Fast-Degradable, Water-Soluble Polycarbonate Functionalized with Tertiary Amine Groups in Backbone. Sep. 13, 2010. Biomacromolecules. vol. 11. pp. 2550-2557. (Year: 2010).*

Sorribes et al. General Catalytic Methylation of Amines with Formic Acid under Mild Reaction Conditions. (2014) Chem. Eur. J. vol. 20. pp. 7878-7883. (Year: 2014).*

Cambre et al. Biomedical applications of boronic acid polymers. Aug. 10, 2011. Polymer. vol. 52. pp. 4631-4643. (Year: 2011).*

Matsumoto et al. New direction in the design of phenylboronate-functionalized polymers for diagnostic and therapeutic applications. Jun. 11, 2014. Polymer Journal. vol. 46. pp. 483-491. (Year: 2014).*

Su et al. Catechol Polymers for pH-Responsive, Targeted Drug Delivery to Cancer Cells. Jul. 13, 2011. Journal of the American Chemical Society. vol. 133. pp. 11850-11853. (Year: 2011).*

Teo et al. pH and redox dual-responsive biodegradable polymeric micelles with high drug loading for effective anticancer drug delivery. Oct. 6, 2016. Nanomedicine: Nanotechnology, Biology, and Medicine. vol. 13. pp. 431-442. (Year: 2016).*

Park et al. Convergent Approach to Boronic Acid Functionalized Polycarbonates: Accessing New Dynamic Material Platforms. Feb. 27, 2017. American Chemical Society. pp. 252-256. (Year: 2017).*

Lewitt, P. A., et al. Subcutaneously administered apomorphine: pharmacokinetics and metabolism. Neurology, Mar. 23, 2004; 62: S8-11. 7 pages.

Bapat, Abhijeet P., et al. "Dynamic-Covalent Macromolecular Stars with Boronic Ester Linkages." J. Am. Chem. Soc. 2011, 133, 19832-19838. 7 pages.

Bull, Steven D. "Exploiting the Reversible Covalent Bonding of Boronic Acids: Recognition, Sensing, and Assembly." Accounts of Chemical Research, vol. 46, No. 2, 2013. 15 pages.

Garcia, Fatima, et al. "Dynamic Covalent Polymers." Journal of Polymer Science, Part A: Polymer Chemistry 2016, 54, 3551-3577. 27 pages.

Kalepu, Sandeep, et al. "Insoluble drug delivery slialegies: review of recent advances and business prospects." Acta Pharmaceutica Sinica B 2015; 5(5):442-453. 12 pages.

Liu, Shaoqiong, et al. "Dual pH-Responsive Shell-Cleavable Polycarbonate Micellar Nanoparticles for in Vivo Anticancer Drug Delivery." ACS Appl. Mater. Interfaces 2018, 10, 19355-19364. 10 pages.

(Continued)

*Primary Examiner* — Tracy Liu

(74) *Attorney, Agent, or Firm* — Amin, Turocy & Watson, LLP

(57) ABSTRACT

Techniques regarding the transportation of molecular cargo across the BBB are provided. For example, one or more embodiments described herein can comprise a chemical compound to facilitate molecular encapsulation of the molecular cargo. The chemical compound can comprise a diblock copolymer having a molecular backbone comprising a polycarbonate structure and a polyethylene glycol structure. Also, the polycarbonate structure can be functionalized with boronic acid.

17 Claims, 16 Drawing Sheets

(56) References Cited

OTHER PUBLICATIONS

Aguirre-Chagala, Yanet Elised, et al. "Synthesis of Copolymers from Phenylboronic Acid-Installed Cyclic Carbonates" ACS Macro Lett. 2014, 3, 353-358. 6 pages.
Aguirre-Chagala, Yanet Elised, et al. "Phenylboronic Acid-Installed Polycarbonates for the pH-Dependent Release of Diol-Containing Molecules." ACS Macro Lett. 2014, 3, 1249-1253. 5 pages.
Brooks, William L. A., et al. "Synthesis and Applications of Boronic Acid-Containing Polymers: From Materials to Medicine." Chem. Rev. 2016, 116, 3, 1375-1397. 23 pages.
Ma, Rujiang, et al. "Phenylboronic acid-based glucose-responsive polymeric nanoparticles: synthesis and applications in drug delivery." Polymer Chemistry, 2014, 5, 1503-1518. 16 pages.
Sun, Xiaolong, et al. "Glucose Sensing in Supramolecular Chemistry." Chem. Rev. 2015, 115, 8001-8037. 37 pages.
Kubo, Yuji, et al. "Hierarchical supramolecules and organization using boronic acids building blocks." Chem. Commun., 2015, 51, 2005-2020. 17 pages.
Pratt, Russell C. "Tagging alcohols with cyclic carbonate: a versatile equivalent of (meth)acrylate for ring-opening polymerization " Chem. Commun., 2008, 114-116. 3 pages.
Yang, Chuan, et al. "The role of non-covalent interactions in anticancer drug loading and kinetic stability of polymeric micelles" Biomaterials 33 (2012) 2971-2979. 9 pages.
Edward, Justin A., et al. "Organocatalytic Synthesis of Quinine-Functionalized Poly(carbonate)s." Biomacromolecules, 2012, 13 (8), pp. 2483-2489. 7 pages.
Suriano, Fabian, et al. "Synthesis, Characterization, and Bioavailability of Mannosylated Shell Cross-Linked Nanoparticles." Biomaterials 31 (2010) 2637-2645. 9 pages.
Voo, Z. X., et al. Antimicrobial coatings against biofilm formation: the unexpected balance between antifouling and bactericidal behavior. Polymer Chemistry, 2016, 7, 656-668. 32 pages.
Matsumoto, Akira, et al. "Glucose-Responsive Polymer Bearing a Novel Phenylborate Derivative as a Glucose-Sensing Moiety Operating at Physiological pH Conditions." Biomacromolecules 2003, 4, 1410-1416. 7 pages.
Matsumoto, Akira, et al. "Swelling and Shrinking Kinetics of Totally Synthetic, Glucose-Responsive Polymer Gel Bearing Phenylborate Derivative as a Glucose-Sensing Moiety." Macromolecules, 2004, 37, 1502-1510. 9 pages.
Li, Yuanpei, et al. "Well-Defined, Reversible Boronate Crosslinked Nanocarriers for Targeted Drug Delivery in Response to Acidic pH Values and cis-Diols." Angewandte Chemie International Edition, 2012, 51, 2864-2869. 6 pages.
Shiino, D., et al. "Controlled release of insulin from boronic acid gel under physiological conditions" Journal of Controlled Release, 1994, 28, 317-318.
Kim, Kyoung Taek "Polymeric Monosaccharide Receptors Responsive at Neutral pH." Journal of the American Chemical Society, 2009, 131, 13908-13909. 2 pages.
Wu, Weitai, et al. "Multifunctional Hybrid Nanogel for Integration of Optical Glucose Sensing and Self-Regulated Insulin Release at Physiological pH." ACS Nano, 2010, 4, 4831-4839. 9 pages.
Krishnamurthy, Sangeetha, et al. "Codelivery of dual drugs from polymeric micelles for simultaneous targeting of both cancer cells and cancer stem cells." Nanomedicine, 2015, 10, 2819-2832. 14 pages.
Kabanov, A.V. "Nanomedicine in the diagnosis and therapy of neurodegenerative disorders." Prog Polym Sci. 2007, 32, 1054-1082. 29 pages.
Mistry, Alpesh, et al. "Nanoparticles for direct nose-to-brain delivery of drugs." Int J Pharm. 2009, 379, 146-157. 12 pages.
Zhao, Ying-Zheng, et al. "Using Gelatin Nanoparticle Mediated Intranasal Delivery of Neuropeptide Substance P to Enhance Neuro-Recovery in Hemiparkinsonian Rats" PoLs One 2016, 11, e0148848. 18 pages.
Kaul, P.N., et al. "Auto-oxidation of Apomorphine." J. Pharm. Sci. 1961, 50, 266-267. 2 pages.
Picada, Jaqueline, N., et al. "Differential mutagenic, antimutagenic and cytotoxic responses induced by apomorphine and its oxidation product, 8-oxo-apomorphine-semiquinone, in bacteria and yeast." Mutation Research/Genetic Toxicology and Environmental Mutagenesis vol. 539, Issues 1-2, Aug. 5, 2003, pp. 29-41. 13 pages.
Dos Santos El-Bacha, Ramon, et al. "Toxic effects of apomorphine on rat cultured neurons and glial C6 cells, and protection with antioxidants." Biochemical Pharmacology vol. 61, Issue 1, Jan. 1, 2001, pp. 73-85. 13 pages.
Pahuja, Richa, et al. "Trans-Blood Brain Barrier Delivery of Dopamine-Loaded Nanoparticles Reverses Functional Deficits in Parkinsonian Rats." ACS Nano 2015, 9, 5, 4850-4871. 22 pages.
Mak, Margaret K., et al. "Long-term effects of exercise and physical therapy in people with Parkinson disease." Nature reviews. Neurology 2017; 13: 689-703. 15 pages.
Pringsheim, Tamara, et al. "The Prevalence of Parkinson's Disease: A Systematic Review and Meta-analysis." Movement disorders 2014; 29: 1583-1590. 8 pages.
Doherty, Gayle Helane, et al. "Homocysteine and Parkinson's Disease: A Complex Relationship." Journal of Neurological Disorders 2013. 9 pages.
Paul, Rajib, et al. "The potential physiological crosstalk and interrelationship between two sovereign endogenous amines, melatonin and homocysteine." Life Sciences 139 (2015) 97-107. 11 pages.
Clarke, Carl E., et al. Systematic review of apomorphine infusion, levodopa infusion and deep brain stimulation in advanced Parkinson's disease. Parkinsonism and Related Disorders 15 (2009) 728-741. 14 pages.
Sridhar, Vinay, et al. Pharmacokinetics and pharmacodynamics of intranasally administered selegiline nanoparticles with improved brain delivery in Parkinson's disease. Nanomedicine: Nanotechnology, Biology and Medicine, 2018. 40 pages.
Gao, Xiaoling, et al. "Brain delivery of vasoactive intestinal peptide enhanced with the nanoparticles conjugated with wheat germ agglutinin following intranasal administration." Journal of Controlled Release 121 (2007) 156-167. 12 pages.
Zhu, K. J., et al. "Synthesis, properties, and biodegradation of poly(1,3-trimethylene carbonate)." Macromolecules 1991,24, 1736-1740. 5 pages.
Leong, Jiayu, et al. "Disease-directed design of biodegradable polymers: Reactive oxygen species and pH-responsive micellar nanoparticles for anticancer drug delivery." Nanomedicine: Nanotechnology, Biology, and Medicine. 2018. 39 pages.
Edward, Justin A., et al. "OOrganocatalytic Synthesis of Quinine-Functionalized Poly(carbonate)s." Biomacromolecules 2012, 13, 2483-2489. 7 pages.
Teo, Jye Yng, et al. "pH and redox dual-responsive biodegradable polymeric micelles with high drug loading for affective anticancer drug delivery." Nanomedicine: Nanotechnology, Biology and Medicine, vol. 13, Issue 2, Feb. 2017. 38 pages.
Wei, Jingjing, et al. "Organocatalytic ring-opening copolymerization of trimethylene carbonate and dithiolane trimethylene carbonate: impact of organocatalysts on copolymerization kinetics and copolymer microstructures." Biomacromolecules. 2018. 24 pages.
Ma, Rujiang, et al. "Iminoboronate-based dual-responsive micelles via subcomponent self-assembly for hydrophilic 1,2-diol-containing drug delivery." RSC Adv., 2017, 7, 21328. 8 pages.
Pratt, Russell C., et al. Exploration, optimization, and application of supramolecular thiourea-amine catalysts for the synthesis of lactide (co)polymers. Macromolecules 2006, 39, 7863-7871, 9 pages.
Wang, Ying, et al. "Biodegradable functional polycarbonate micelles for controlled release of amphotericin B." Acta Biomaterialia, 2016 10 pages.
Obuobi, Sybil, et al. "Phenylboronic Acid Functionalized Polycarbonate Hydrogels for Controlled Release of Polymyxin B in Pseudomonas Aeruginosa Infected Burn Wounds." Adv. Healthcare Mater. 2018, 1701388. 8 pages.
Ryu, Ji Hyun, et al. "Catechol-Functionalized Chitosan/Pluronic Hydrogels for Tissue Adhesives and Hemostatic Materials." Biomacromolecules, 2011, 12 (7), pp. 2653-2659. 7 pages.
Wohlfart, Stefanie, et al. "Transport of drugs across the blood-brain barrier by nanoparticles." Journal of Controlled Release, vol. 161, Issue 2, Jul. 20, 2012, pp. 264-273. 10 pages.

(56) References Cited

OTHER PUBLICATIONS

Farokhzad, Omid, C., et al. "Targeted nanoparticle-aptamer bioconjugates for cancer chemotherapy in vivo." PNAS, vol. 103, No. 16, 6315-6320, Apr. 18, 2006. 6 pages.

* cited by examiner

400

404

402

100

600

106

402

602

900

1100

1200

1300

CONJUGATING A CHEMICAL COMPOUND TO A COPOLYMER VIA AN ACIDITY-SENSITIVE COVALENT BORONATE ESTER BOND, WHEREIN THE COPOLYMER COMPRISES A POLYCARBONATE STRUCTURE FUNCTIONALIZED WITH BORONIC ACID, AND WHEREIN THE ACIDITY-SENSITIVE COVALENT BORONATE ESTER BOND IS FORMED BETWEEN THE BORONIC ACID AND A CATECHOL MOIETY OF THE CHEMICAL COMPOUND

1302

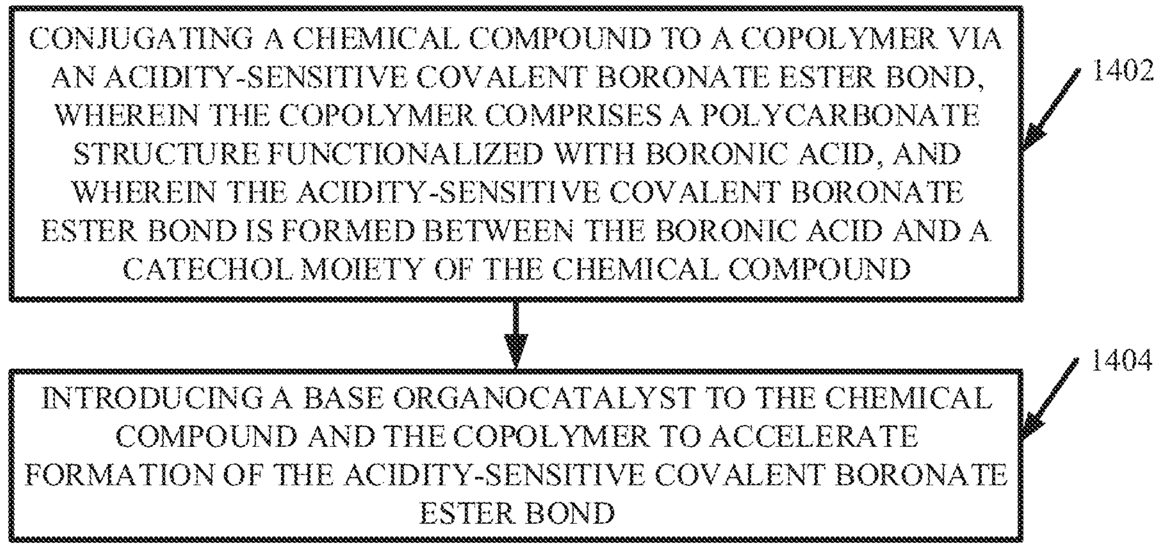

```
┌─────────────────────────────────────────────────────────┐
│ CONJUGATING A CHEMICAL COMPOUND TO A COPOLYMER VIA      │
│ AN ACIDITY-SENSITIVE COVALENT BORONATE ESTER BOND,      │ ← 1402
│ WHEREIN THE COPOLYMER COMPRISES A POLYCARBONATE         │
│ STRUCTURE FUNCTIONALIZED WITH BORONIC ACID, AND         │
│ WHEREIN THE ACIDITY-SENSITIVE COVALENT BORONATE         │
│ ESTER BOND IS FORMED BETWEEN THE BORONIC ACID AND A     │
│ CATECHOL MOIETY OF THE CHEMICAL COMPOUND                │
└─────────────────────────────────────────────────────────┘
                             │
                             ▼
┌─────────────────────────────────────────────────────────┐
│ INTRODUCING A BASE ORGANOCATALYST TO THE CHEMICAL       │ ← 1404
│ COMPOUND AND THE COPOLYMER TO ACCELERATE                │
│ FORMATION OF THE ACIDITY-SENSITIVE COVALENT BORONATE    │
│ ESTER BOND                                              │
└─────────────────────────────────────────────────────────┘
```

1500

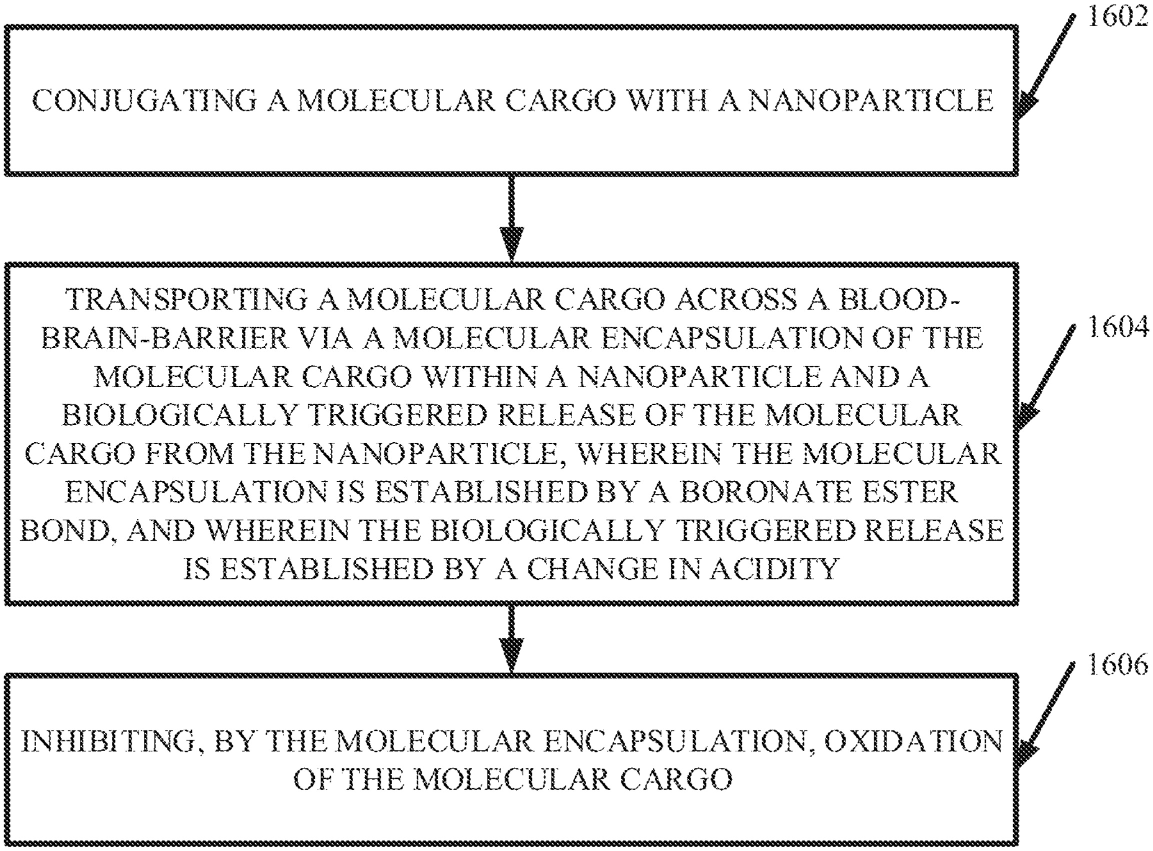

1602 — CONJUGATING A MOLECULAR CARGO WITH A NANOPARTICLE

1604 — TRANSPORTING A MOLECULAR CARGO ACROSS A BLOOD-BRAIN-BARRIER VIA A MOLECULAR ENCAPSULATION OF THE MOLECULAR CARGO WITHIN A NANOPARTICLE AND A BIOLOGICALLY TRIGGERED RELEASE OF THE MOLECULAR CARGO FROM THE NANOPARTICLE, WHEREIN THE MOLECULAR ENCAPSULATION IS ESTABLISHED BY A BORONATE ESTER BOND, AND WHEREIN THE BIOLOGICALLY TRIGGERED RELEASE IS ESTABLISHED BY A CHANGE IN ACIDITY

1606 — INHIBITING, BY THE MOLECULAR ENCAPSULATION, OXIDATION OF THE MOLECULAR CARGO

BIODEGRADABLE FUNCTIONAL POLYCARBONATE NANOPARTICLE CARRIES FOR DELIVERING MOLECULAR CARGO

BACKGROUND

The subject disclosure relates to the delivery of one or more sensitive chemical compounds across the blood-brain barrier using molecular encapsulation, and more specifically, to one or more biodegradable copolymer carriers comprising a polycarbonate structure functionalized with boronic acid via a pH-sensitive covalent boronate ester bond.

Parkinson's disease is a progressive, neurodegenerative disorder with symptoms reflecting various impairments and functional limitations (e.g., postural instability, immobility and falls) and is the second most common neurodegenerative disorder globally. Orally taking levodopa is the most common treatment for Parkinson's disease. However, long term users of levodopa can have an elevated level of homocysteine, which can further cause neurotoxicity through oxidative stress. Very often, motor movements will become increasingly refractory to levodopa.

Therefore, infusion therapy (e.g., using apomorphine ("AMP")) and/or stereostatic surgery can become a prominent consideration in treatment. AMP is a potent dopamine agonist; however, it cannot be administered orally due to its high first pass hepatic metabolism and short half-life. The rate of uptake after subcutaneous injection is dependent on location, body temperature, depth of injection and body fat level. Thus, the therapeutic efficacy of various chemical compounds used to treat neurodegenerative disorders such as Parkinson's disease can be impaired by the compounds' degradation by the monoamine oxidase enzyme and oxidation and/or difficulty crossing the blood-brain barrier ("BBB").

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, chemical compounds and/or methods regarding the delivery of one or more sensitive chemical compounds across the BBB using molecular encapsulation are described.

According to an embodiment, a chemical compound is provided. The chemical compound can comprise a diblock copolymer having a molecular backbone comprising a polycarbonate structure and a polyethylene glycol structure. The polycarbonate structure can be functionalized with boronic acid. An advantage of such a chemical compound can be that the chemical compound can be biodegradable and/or biocompatible while enabling the molecular encapsulation of one or more therapeutic chemical compounds.

In some examples, the boronic acid can be an arylboronic acid. An advantage of such a chemical compound can be that one or more aryl groups of the arylboronic acid can be electron withdrawing groups to facilitate formation of a boronate ester bond from the arylboronic acid.

According to an embodiment, a chemical compound is provided. The chemical compound can comprise a copolymer having a molecular backbone comprising a polyethylene glycol structure, a first polycarbonate structure, and a second polycarbonate structure. The first polycarbonate structure can be functionalized with boronic acid and the second polycarbonate structure can be covalently bonded to an amino functional group. An advantage of such a chemical compound can be that the amino functional group can serve as an integrated catalyst to facilitate one or more chemical interactions between the chemical compound and one or more molecular cargos that can be subject to molecular encapsulation.

In some examples, the boronic acid can be an arylboronic acid, and the amino functional group can comprise a tertiary amine. An advantage of such a chemical compound can be that the tertiary amine can serve as a catalyst for one or more covalent bonds regarding a neighboring boron of the boronic acid.

According to an embodiment, method is provided. The method can comprise conjugating a chemical compound to a copolymer via an acidity-sensitive covalent boronate ester bond. The copolymer can comprise a polycarbonate structure functionalized with boronic acid. Also, the acidity-sensitive covalent boronate ester bond can be formed between the boronic acid and a catechol moiety of the chemical compound. An advantage of such a method can be that the conjugation can be reversible based on an acidity of the environment surrounding the chemical compound.

In some examples, the method can further comprise introducing a base organocatalyst to the chemical compound and the copolymer to accelerate formation of the acidity-sensitive covalent boronate ester bond. An advantage of such a method can be that the base organocatalyst can serve to lower a negative base-10 logarithm of the acid dissociation constant ("pKa") value of the boronic acid, and thereby accelerate formation of the acidity-sensitive covalent boronate ester bond.

According to an embodiment a chemical compound is provided. The chemical compound can comprise a therapeutic compound bonded to a copolymer by an acidity-sensitive covalent boronate ester bond. The copolymer can comprise a polycarbonate structure functionalized with boronic acid. Also, the acidity-sensitive covalent boronate ester bond can be formed between the boronic acid and a catechol moiety of the therapeutic compound. An advantage of such a chemical compound can be that release of the therapeutic compound can be triggered biologically.

In some examples, the therapeutic compound can be apomorphine. An advantage of such a chemical compound can be that the chemical compound can be used to treat one or more neurodegenerative disorders.

According to an embodiment a method is provided. The method can comprise transporting a molecular cargo across a blood-brain-barrier via a molecular encapsulation of the molecular cargo within a nanoparticle and a biologically triggered release of the molecular cargo from the nanoparticle. The molecular encapsulation can be established by a boronate ester bond, and the biologically triggered release can be established by a change in acidity. An advantage of such a method can be that the molecular encapsulation can inhibit oxidation of the molecular cargo.

In some examples, wherein the biologically triggered release is established in a presence of an environment having an acidity of less than or equal to 6.8 pH. An advantage of such a method can be that that premature release of the molecular cargo can be mitigated by the environmental conditions in which the molecular encapsulation is distributed.

BRIEF DESCRIPTION OF THE DRAWINGS

FIG. 14 illustrates a flow diagram of an example, non-limiting method that can facilitate conjugating one or more molecular cargos with the first polymer and/or the second polymer in accordance with one or more embodiments described herein.

FIG. 16 illustrates a flow diagram of an example, non-limiting method that can facilitate transporting a molecular cargo across the BBB in accordance with one or more embodiments described herein.

DETAILED DESCRIPTION

Figure 1A:
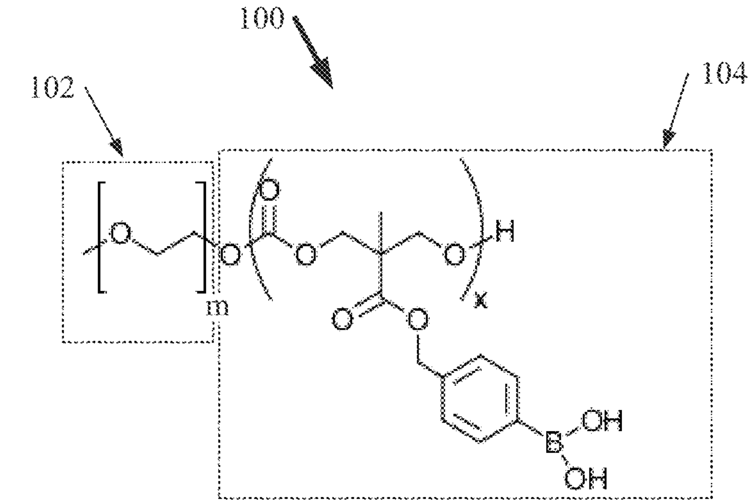
FIG. 1A illustrates a diagram of an example, non-limiting first polymer that can facilitate transportation of a molecular cargo across the BBB in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Given the above problems with conventional methods to transport molecular cargo (e.g., therapeutic chemical compounds) across the BBB; the present disclosure can be implemented to produce a solution to one or more of these problems in the form of one or more polymers that can encapsulate one or more molecular cargos and/or transport the one or more molecular cargos across the BBB. For example, the various polymers described herein can protect one or more molecular cargos from oxidation, which can typically render the one or more molecular cargos toxic in a biological environment. Additionally, the one or more loaded polymers described herein (e.g., polymers conjugated with one or more molecular cargos) can have a size less than 400 nanometers (nm) to facilitate transportation across the BBB. Further, the various polymers described herein can form one or more dynamic covalent bonds with the one or more molecular cargos to establish a release of the one or molecular cargos that is biologically triggered.

Various embodiments described herein can comprise chemical compounds and/or methods regarding the transportation of one or more molecular cargos across the BBB. For example, one or more embodiments can regard conjugating one or more molecular cargos (e.g., one or more therapeutic chemical compounds, such as AMP) to biodegradable diblock copolymers of poly(ethylene glycol) ("PEG") and a boronic acid-functionalized polycarbonate via a pH-sensitive covalent boronate ester bond formed between the boronic acid and the catechol moiety in the molecular cargo. Various conditions including use of base, reaction time and initial chemical compound loading can be optimized to achieve high chemical compound conjugation degree and mitigate polymer degradation caused by one or more amine groups in the molecular cargo. For instance, the presence of a basic organocatalyst can accelerate molecular cargo conjugation to the polymer carrier and/or allow for maximum conjugation of about 75% with an initial loading ratio of molecular cargo to the polymer carrier at 3:1 within 5 minutes. Additionally, in one or more embodiments, one or more amine groups can be incorporated to polycarbonate block, and/or serve as a catalyst to accelerate conjugation. The conjugated polymers can self-assemble into nanoparticles with sizes below 110 nm and narrow size distribution as evidenced by dynamic light scattering and transmission electron microscopy ("TTEM"). In vitro molecular cargo release from the nanoparticles can exhibit a pH-dependence. For example, at pH 7.4, the release of molecular cargo can be minimal, while in an acidic environment (e.g., comprising endolysosomes) rapid molecular cargo release can be exhibited (e.g., about 75% of molecular cargo released over 48 hours). Molecular encapsulation of the one or more molecular cargos into the nanoparticles can protected the one or more molecular cargos from oxidization. Moreover, an accumulation of the nanoparticles in brain tissue can be observed after intranasal delivery. The loaded nanoparticles described herein can have potential for use in the treatment of one or more neurodegenerative disorders (e.g., Parkinson's disease).

FIG. 1A illustrates a diagram of an example, non-limiting first polymer carrier 100 that can encapsulate one or more molecular cargos via a dynamic covalent bond to facilitate transportation of the one or more molecular cargos across the BBB in accordance with one or more embodiments described herein. As shown in FIG. 1A, the first polymer carrier 100 can be a diblock copolymer having a molecular backbone comprising one or more PEG structures 102 bonded to one or more first polycarbonate structures 104. Also shown in FIG. 1A, "m" can be an integer greater than or equal to 45 and less than or equal to 454, and/or "x" can be an integer greater than or equal to 2 and less than or equal to 100.

In one or more embodiments, the one or more PEG structures 102 can have a molecular weight (e.g., at least partially established by the value of "m") greater than or equal to 2,000 daltons (Da) and less than or equal to 20,000 Da (e.g., 10,000 Da). Additionally, the one or more first polycarbonate structures 104 can be functionalized with boronic acid (e.g., as shown in FIG. 1A). In various embodiments, the boronic acid can be an arylboronic acid, such as phenylboronic acid (e.g., as shown in FIG. 1A). The first polymer carrier 100 can be biodegradable and/or biocompatible. Further, the first polymercarrier 100 can have a particle size greater than or equal to 15 nm and less than or equal to 400 nm.

Figure 1B:
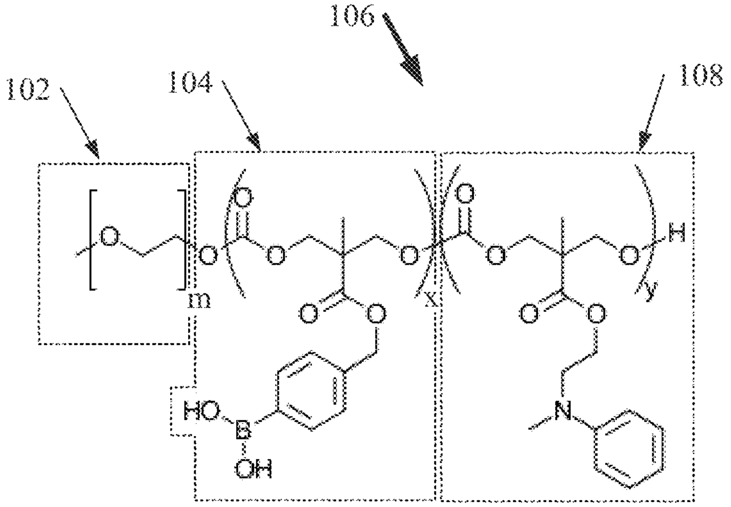
FIG. 1B illustrates a diagram of an example, non-limiting second polymer that can facilitate transportation of a molecular cargo across the BBB in accordance with one or more embodiments described herein.

FIG. 1B illustrates a diagram of an example, non-limiting second polymer carrier 106 that can encapsulate one or more molecular cargos via a dynamic covalent bond to facilitate transportation of the one or more molecular cargos across the BBB in accordance with one or more embodiments described herein. Repetitive description of like elements employed in other embodiments described herein is omitted for sake of brevity. As shown in FIG. 1B, the second polymer carrier 106 can be a triblock copolymer having a molecular backbone comprising the one or more PEG structures 102 bonded to the one or more first polycarbonate structures 104 and/or one or more second polycarbonate structures 108. Also shown in FIG. 1B, "m" can be an integer greater than or equal to 45 and less than or equal to 454, "x" can be an integer greater than or equal to 2 and less than or equal to 50, and/or "y" can be an integer greater than or equal to 2 and less than or equal to 50.

In one or more embodiments, the one or more second polycarbonate structures 108 can be functionalized with one or more amino groups comprising one or more tertiary amines (e.g., as shown in FIG. 1B). For example, the one or more second polycarbonate structures 108 can be functionalized with one or more aniline structures comprising a tertiary amine (e.g., dimethylaniline, as shown in FIG. 1B).

Figure 2:
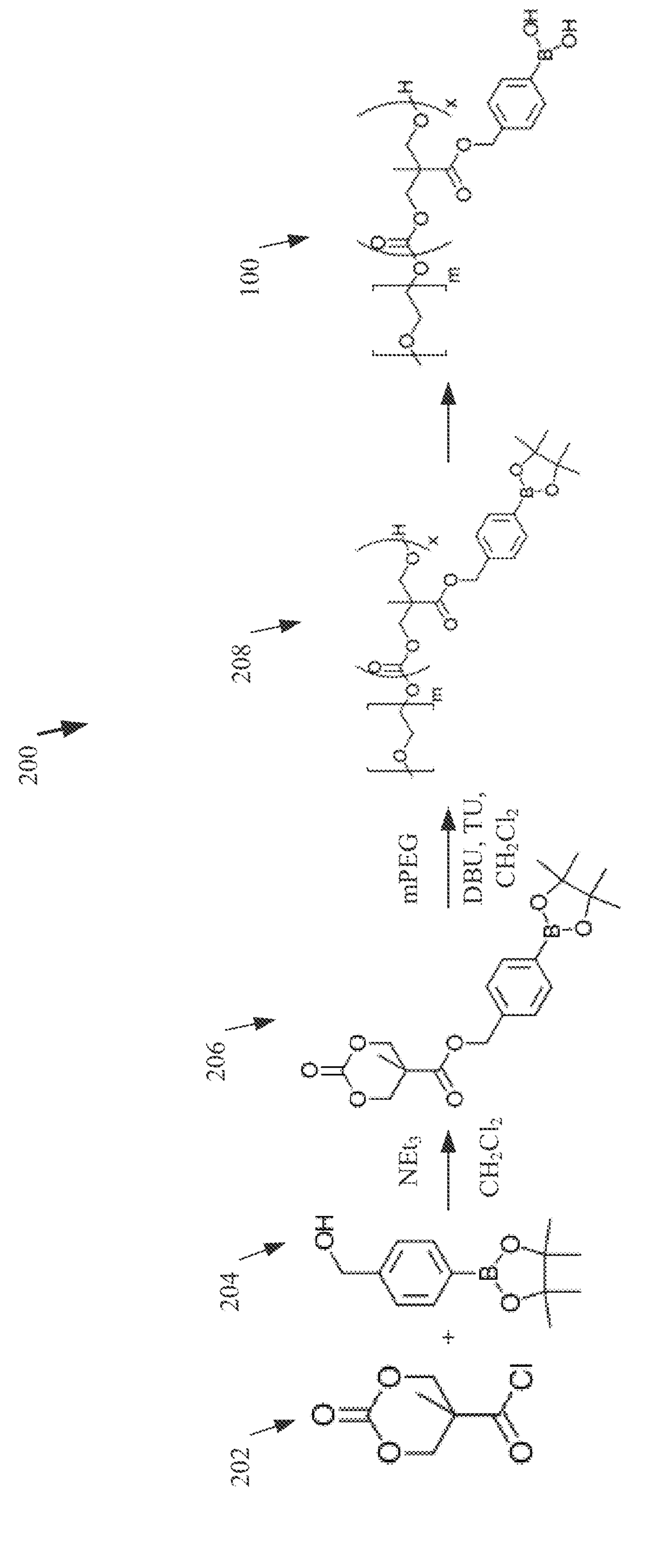
FIG. 2 illustrates a diagram of an example, non-limiting polymerization scheme to facilitate polymerization of the first polymer that can facilitate transportation of a molecular cargo across the BBB in accordance with one or more embodiments described herein.

FIG. 2 illustrates a diagram of an example, non-limiting first polymerization scheme 200 that can facilitate synthesis of the one or more first polymer carriers 100 in accordance with one or more embodiments described herein. Repetitive description of like elements employed in other embodiments described herein is omitted for sake of brevity. In various embodiments, the first polymerization scheme 200 can comprise an organocatalytic ring-opening polymerization ("OROP"). As shown in FIG. 2, the first polymerization scheme 200 can begin by reacting a carbonate monomer 202 with a boronic acid pinacol ester monomer 204 with a solvent in the presence of an organocatalyst. Also shown in FIG. 2, "m" can be an integer greater than or equal to 45 and less than or equal to 454, and/or "x" can be an integer greater than or equal to 2 and less than or equal to 100.

The carbonate monomer 202 can comprise be functionalized with a halogen. For example, the carbonate monomer 202 can be a cyclic carbonate functionalized with chlorine (e.g., as shown in FIG. 2). For instance, the carbonate monomer 202 can be 5-chlorocarboxy-5-methyl-1,3-dioxan-2-one ("MTC-Cl"), as shown in FIG. 2. The boronic acid pinacol ester monomer 204 can comprise one or more hydroxyl groups bound to a boronic acid pinacol ester structure. Further, the boronic acid pinacol ester structure can comprise an arylboronic acid sub-structure. For instance, the boronic acid pinacol ester monomer 204 can be 4-hydroxymethyl phenylboronic acid pinacol ester, wherein a hydroxyl group can be bound to the phenylboronic acid sub-substructure (e.g., as shown in FIG. 2). Example solvents can include, but are not limited to: dichloromethane ("$CH_2Cl_2$") (e.g., as shown in FIG. 2), tetrahydrofuran ("THF"), acetonitrile, acetone, toluene, a combination thereof and/or the like. Additionally, example organocatalysts that can facilitate the first polymerization scheme 200 can be one or more amine compounds, including, but are not limited to: triethylamine ("$Net_3$") (e.g., as shown in FIG. 2), a 1,8-diazabicyclo[5.4.0]undec-7-ene ("DBU") and thiourea combination, a combination thereof, and/or the like.

Reacting the carbonate monomer 202 and the boronic acid pinacol ester monomer 204 can produce a cyclic carbonate monomer 206. The cyclic carbonate monomer 206 can be a pinacol protected boronic acid-functionalized cyclic carbonate. For example, the cyclic carbonate monomer 206 can be a pinacol protected arylboronic acid-functionalized cyclic carbonate, such as the pinacol protected phenylboronic acid-functionalized cyclic carbonate shown in FIG. 2.

As shown in FIG. 2, the cyclic carbonate monomer 206 can be further polymerized with a methoxy(polyethylene glycol) ("mPEG") initiator to form a first intermediate polymer 208, which can be a diblock copolymer comprising a pinacol protected boronic acid-functionalized polycarbonate structure. The mPEG initiator can be capped with one or more hydroxyl groups. Further, the mPEG initiator can have an exemplary molecular weight greater than or equal to 2,000 Da and less than or equal to 20,000 Da (e.g., 10,000 Da). The cyclic carbonate monomer 206 and the mPEG initiator can be polymerized in the presence of one or more organocatalysts and/or solvents. Example organocatalysts can include, but are not limited to: DBU, N-(3,5-Trifuluoromethyl)phenyl-N'-cyclohexylthiourea ("TU"), a combination thereof, and/or the like. Example solvents can include, but are not limited to: dichloromethane ("$CH_2Cl_2$"), THF, acetonitrile, toluene, a combination thereof and/or the like. For instance, the cyclic carbonate monomer 206 and the mPEG initiator can be polymerized in the presence DBU, TU, and/or $CH_2Cl_2$ as shown in FIG. 2. In one or more embodiments, the first intermediate polymer 208 can be a diblock copolymer comprising PEG bonded to a pinacol protected boronic acid-functionalized polycarbonate structure, such as a pinacol protected phenylboronic acid-functionalized polycarbonate structure (e.g., as shown in FIG. 2).

Additionally, the first intermediate polymer 208 can be deprotonated to form the first polymer carrier 100. For example, the boronate ester bond formed with the pinacol can be deprotonated to form the boronic acid structure of the first polymer carrier 100. In other words, the deprotonation can form one or more hydroxyl groups from the boronate ester bond.

To exemplify various features of the first polymerization scheme 200, the following exemplary polymerization procedure can be performed to synthesize the first polymer carrier 100. One of ordinary skill in the art will readily recognize that the following polymerization procedure is exemplary and/or one or more alternatives to the materials and/or chemical compounds described below can be utilized in accordance with the various features of the first polymerization scheme 200 described herein.

For instance, a mPEG initiator (e.g., having a molecular weight of 10,000 Da and a polydispersity index ("PDI") of 1.10) can be lyophilized and transferred to a glove-box one day prior to use. Additionally, DBU can be dried over calcium hydride ("$CaH_2$") overnight. The dried DBU can be obtained after vacuum distillation, and then transferred to a glove-box prior to use. Further, co-catalyst, TU can be synthesized as known in the art.

MTC-CL (e.g., the carbonate monomer 202) can be synthesized by reacting 5-Methyl-5-carboxyl-1,3-dioxan-2-one ("MTC-OH") with oxalyl chloride. MTC-Cl can then be reacted with 4-hydroxymethyl phenylboronic acid pinacol ester (e.g., the boronic acid pinacol ester monomer 204) in dry $CH_2Cl_2$ in the presence of triethylamine to produce pinacol protected phenylboronic acid-functionalized cyclic carbonate monomer ("MTC-PPB") (e.g., the cyclic carbonate monomer 206).

In a glove-box, 0.222 grams (g) (e.g., 0.022 millimoles (mmol)) of 10 kiloDa mPEG-OH initiator and 0.376 g (e.g., 1 mmol) of MTC-PPB can be charged in a 20 milliliter (mL) glass vial equipped with a stir bar. Dichloromethane can be added, and the monomer concentration can be adjusted to 2 molar (M). Once the mPEG-OH initiator and MTC-PPB monomer are completely dissolved, 8.3 microliters (μL) (e.g., 0.06 mmol) of DBU can be added to initiate the polymerization. After about 3.5 hours of stirring at room temperature, the reaction can be quenched with 30 milligrams (mg) of benzoic acid. Subsequently, the intermediate PEG-P(MTC-PPBA) P(MTC-PPBA) (e.g., the first intermediate polymer 208) can be purified via precipitation twice in cold diethyl ether, and can be dried on a vacuum line until a constant weight was achieved. A proton nuclear magnetic resonance (e.g., $^1H$ NMR) regarding the purified P(MTC-PPBA) (e.g., the first intermediate polymer 208) can observe the following results: δ7.83-7.27 (m, 48H, $—C_6H_4B═$), 5.23-5.02 (m, 24H, $—CH_2C_6H_4—$), 4.49-4.13 (m, 48H, $—OCOOCH_2—$), 3.84-3.43 (m, 908H, $—OCH_2CH_2—$ from 10 kDa PEG), 3.38 (s, 3H, $CH_3$-PEG-), 1.39-1.27 (m, 144H, 4×$CH_3$ on the protecting group), 1.26-1.16 (m, 36H, $—CH_3$ on cyclic carbonate). Additionally, the purified P(MTC-PPBA) (e.g., the first intermediate polymer 208) can have a molecular weight of 12.5 kiloDa and/or a PDI of 1.16.

The protected P(MTC-PPBA) (e.g., the first intermediate polymer 208) can then be deprotected by dissolving in 14 mL of methanol and tetrahydrofuran ("THF") (e.g., in a 1:1 ratio) and 10 equivalents (e.g., with respect to moles of protected phenylboronic pinacol pendant groups) of benzene-1,4-diboronic acid, and DOWEX® 50W-X2 acidic resins can be added to a 50 mL flask containing the protected P(MTC-PPBA) polymer. The flask can subsequently be heated to 50 degrees Celsius (° C.) with overnight stirring. The solvents can be removed under vacuum and the deprotected polymer can be dissolved in 10 mL of isopropanol and acetonitrile (e.g., in a ratio of 1:1) and placed within a dialysis bag of 1000 molecular weight cut-off. Dialysis can be carried out for the next 2 days at room temperature using 1:1 isopropanol and acetonitrile. Finally, the solvents can be removed and the first polymercarrier 100 can be lyophilized to obtain an off-white polymer. A $^1H$ NMR regarding the first polymercarrier 100 can observe the following results: δ8.22-7.88 (m, 24H, $—B(OH)_2$), 7.84-7.15 (m, 48H, $—C_6H_4B═$), 5.23-4.96 (m, 24H, $—CH_2C_6H_4—$), 4.46-4.02 (m, 48H, $—OCOOCH_2—$), 3.71.-3.14 (m, 909H, $—OCH_2CH_2—$ from 10 kiloDa PEG), 3.23 (s, 3H, $CH_3$-PEG-), 1.25-1.05 (m, 36H, $—CH_3$ on the polymer backbone).

Therefore, in one or more embodiments the first polymercarrier 100 can be synthesized via a metal-free OROP of MTC-PPB using MPEG of 10 kiloDa as a macroinitiator in the presence of the co-catalysts DBU and/or TU for 3.5 hours. $^1H$ NMR integration values of monomer relative to the PEG initiator can confirm controlled polymerization and predictable molecular weight via initial monomer to initiator feed ratio (e.g., the degree of polymerization ("DP") can equal 12) based on the methylene peak belonging to the pendant protected phenylboronic esters at $^1H$ NMR region 5.23-5.02 parts per million ("ppm") and the methylene peak of PEG. In addition, the $^1H$ NMR analysis displayed all the peaks associated with both initiator and monomers. Further, from gel permeation chromatography ("GPC") analysis, the protected P(MTC-PPBA) can have a narrow molecular weight distribution with a PDI of 1.16. The pinacol protected phenylboronic acid groups in the first polymercarrier 100 can be subsequently deprotected, without hydrolytic cleavage to the polycarbonate backbone (e.g., DP can remain as 12 based on methylene protons of the phenylboronic acid between 5.25-5.01 ppm), and the $^1H$ NMR spectrum showed the disappearance of the methyl protons from the pinacol protecting groups in the deprotected first polymer carrier 100. In addition, the presence of a new distinct peak at 8.05 ppm confirmed the presence of hydroxyl groups, which correlates to the deprotected phenylboronic acid pendant groups.

Figure 3:
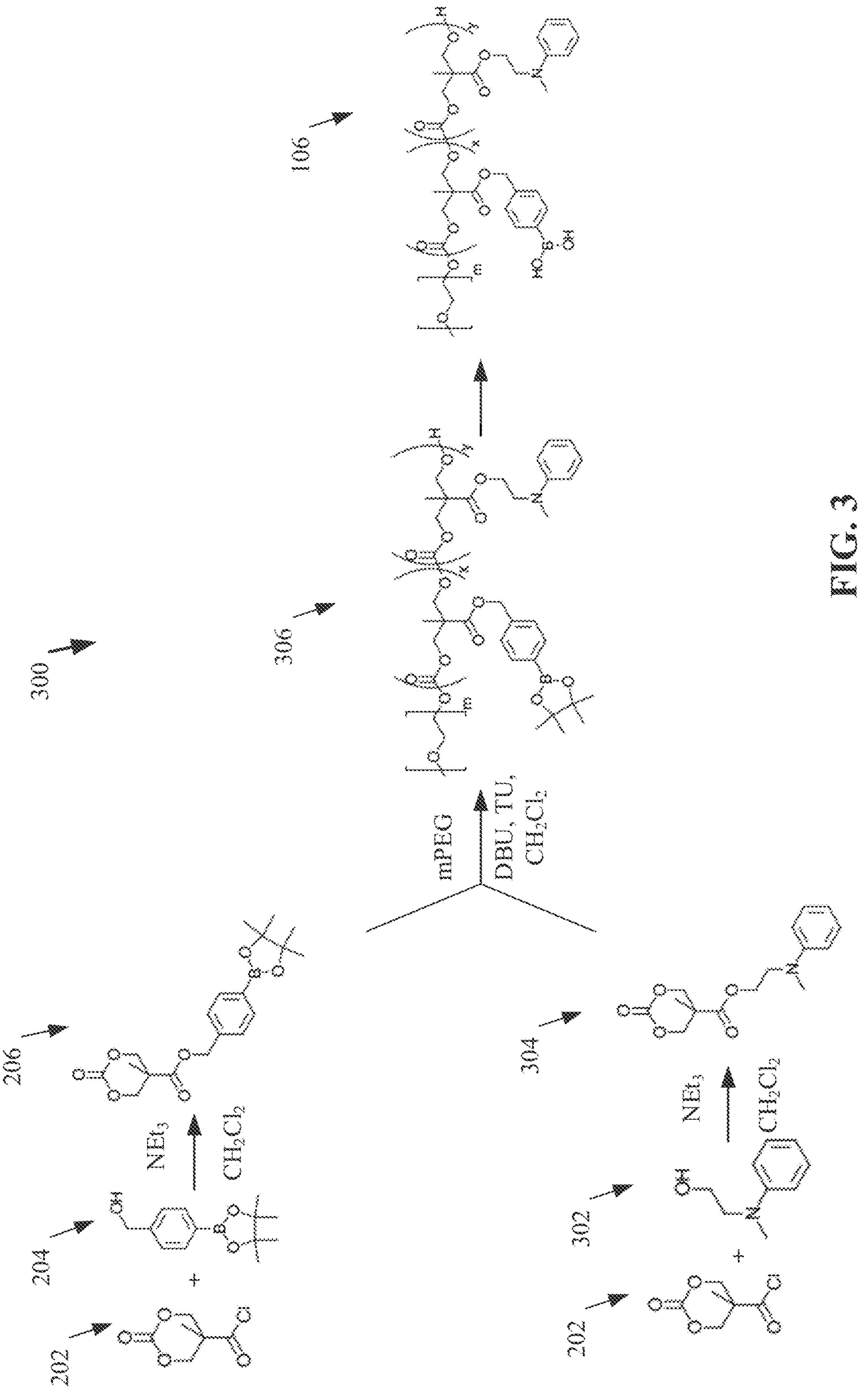
FIG. 3 illustrates a diagram of an example, non-limiting polymerization scheme to facilitate polymerization of the second polymer that can facilitate transportation of a molecular cargo across the BBB in accordance with one or more embodiments described herein.

FIG. 3 illustrates a diagram of an example, non-limiting second polymerization scheme 300 that can facilitate synthesis of the one or more second polymer carriers 106 in accordance with one or more embodiments described herein. Repetitive description of like elements employed in other embodiments described herein is omitted for sake of brevity. In various embodiments, the second polymerization scheme 300 can comprise an organocatalytic ring-opening polymerization. As shown in FIG. 3, the second polymerization scheme 300 can begin by reacting a carbonate monomer 202 with a boronic acid pinacol ester monomer 204 with a solvent in the presence of an organocatalyst. Also shown in FIG. 3, "m" can be an integer greater than or equal to 45 and less than or equal to 454, "x" can be an integer greater than or equal to 2 and less than or equal to 50, and/or "y" can be an integer greater than or equal to 2 and less than or equal to 50.

As described with regards to the second polymerization scheme 300, the carbonate monomer 202 can comprise be functionalized with a halogen. For example, the carbonate monomer 202 can be a cyclic carbonate functionalized with chlorine (e.g., as shown in FIG. 3). For instance, the carbonate monomer 202 can be MTC-Cl, as shown in FIG. 3. The boronic acid pinacol ester monomer 204 can comprise one or more hydroxyl groups bound to a boronic acid pinacol ester structure. Further, the boronic acid pinacol ester structure can comprise an arylboronic acid sub-structure. For instance, the boronic acid pinacol ester monomer 204 can be 4-hydroxymethyl phenylboronic acid pinacol ester, wherein a hydroxyl group can be bound to the phenylboronic acid sub-substructure (e.g., as shown in FIG. 3). Example solvents can include, but are not limited to: dichloromethane ("$CH_2Cl_2$") (e.g., as shown in FIG. 3), THF, acetonitrile, acetone, toluene, a combination thereof and/or the like. Additionally, example organocatalysts that can facilitate the second polymerization scheme 300 can include, but are not limited to: triethylamine ("$Net_3$") (e.g., as shown in FIG. 3), tertiary amines, triethylamine, pyridine, a combination thereof, and/or the like.

Reacting the carbonate monomer 202 and the boronic acid pinacol ester monomer 204 can produce a cyclic carbonate monomer 206. The cyclic carbonate monomer 206 can be a pinacol protected boronic acid-functionalized cyclic carbonate. For example, the cyclic carbonate monomer 206 can be a pinacol protected arylboronic acid-functionalized cyclic carbonate, such as the pinacol protected phenylboronic acid-functionalized cyclic carbonate shown in FIG. 3.

Additionally, the second polymerization scheme 300 can comprise reacting the carbonate monomer 202 with an amine monomer 302 to form an amino-functionalized cyclic carbonate monomer 304. The amine monomer 302 can comprise one or more hydroxyl groups and one or more primary amines, secondary amines, and/or tertiary amines (e.g., as shown in FIG. 3). Further, the amine monomer 302 can comprise one or more aniline structures. For example, in one or more embodiments the amine monomer 302 can be 2-(methylphenylamino) ethanol (e.g., as shown in FIG. 3). In one or more embodiments, the amino-functionalized cyclic carbonate monomer 304 can be an aniline-functionalized cyclic carbonate monomer, such as 2-methylphenylamino functionalized cyclic carbonate monomer ("MTC-MPA"). The carbonate monomer 202 and the amine monomer 302 can be reacted with a solvent in the presence of an organocatalyst. Example solvents can include, but are not limited to: dichloromethane ("$CH_2Cl_2$") (e.g., as shown in FIG. 3), THF, acetonitrile, acetone, toluene, a combination thereof and/or the like. Additionally, example organocatalysts that can facilitate the second polymerization scheme 300 can include, but are not limited to: triethylamine ("$Net_3$") (e.g., as shown in FIG. 3), DBU, triazabicyclodecene ("TBD"), a combination thereof, and/or the like.

As shown in FIG. 3, the cyclic carbonate monomer 206 and the amino-functionalized cyclic carbonate monomer 304 can be further polymerized with a mPEG initiator to form a second intermediate polymer 306, which can be a triblock copolymer comprising a pinacol protected boronic acid-functionalized polycarbonate structure and an amino-functionalized polycarbonate structure. The mPEG initiator can be capped with one or more hydroxyl groups. Further, the mPEG initiator can have an exemplary molecular weight greater than or equal to 2,000 Da and less than or equal to 20,000 Da (e.g., 10,000 Da). The cyclic carbonate monomer 206, the amino-functionalized cyclic carbonate monomer 304, and the mPEG initiator can be polymerized in the presence of one or more organocatalysts and/or solvents. Example organocatalysts can include, but are not limited to: DBU, TU, TBD, 4-dimethylaminopyridine ("DMAP"), a combination thereof, and/or the like. Example solvents can include, but are not limited to: dichloromethane ("$CH_2Cl_2$"), THF, acetonitrile, acetone, toluene, a combination thereof and/or the like. For instance, the cyclic carbonate monomer 206, the amino-functionalized cyclic carbonate monomer 304, and the mPEG initiator can be polymerized in the presence DBU, TU, and/or $CH_2Cl_2$ as shown in FIG. 3. In one or more embodiments, the second intermediate polymer 306 can be a triblock copolymer comprising PEG bonded to a pinacol protected boronic acid-functionalized polycarbonate structure and/or an amino-functionalized polycarbonate structure, such as a pinacol protected phenylboronic acid-functionalized polycarbonate structure and/or a 2-methylphenylamino-functionalized polycarbonate structure (e.g., as shown in FIG. 3).

Additionally, the second intermediate polymer 306 can be deprotonated to form the second polymer carrier 106. For example, the boronate ester bond formed with the pinacol can be deprotonated to form the boronic acid structure of the second polymer carrier 106. In other words, the deprotonation can form one or more hydroxyl groups from the boronate ester bond.

To exemplify various features of the second polymerization scheme 300, the following exemplary polymerization procedure can be performed to synthesize the second polymer carrier 106. One of ordinary skill in the art will readily recognize that the following polymerization procedure is exemplary and/or one or more alternatives to the materials and/or chemical compounds described below can be utilized in accordance with the various features of the second polymerization scheme 300 described herein.

For instance, a mPEG initiator (e.g., having a molecular weight of 10,000 Da and a polydispersity index ("PDI") of 1.10) can be lyophilized and transferred to a glove-box one day prior to use. Additionally, DBU can be dried over $CaH_2$ overnight. The dried DBU can be obtained after vacuum distillation, and then transferred to a glove-box prior to use. Further, co-catalyst, TU can be synthesized as known in the art.

MTC-CL (e.g., the carbonate monomer 202) can be synthesized by reacting 5-Methyl-5-carboxyl-1,3-dioxan-2-one ("MTC-OH") with oxalyl chloride. MTC-Cl can then be reacted with 4-hydroxymethyl phenylboronic acid pinacol ester (e.g., the boronic acid pinacol ester monomer 204) in dry $CH_2Cl_2$ in the presence of triethylamine to produce pinacol protected phenylboronic acid-functionalized cyclic carbonate monomer ("MTC-PPB") (e.g., the cyclic carbonate monomer 206).

Additionally, MTC-CL (e.g., 3.08 g,19.3 mmol) (e.g., the carbonate monomer 202) can be dissolved in dry dichloromethane (e.g., 50 mL), followed by immersing the flask in an ice bath at 0° C. A mixture of 2-(methylphenylamino) ethanol (e.g., 2.70 g, 17.88 mmol) (e.g., the amine monomer 302) and triethylamine (e.g., 1.77 mL, 19.3 mmol) can be dissolved in dry $CH_2Cl_2$ (e.g., 50 mL), which can be added dropwise to the flask over a duration of 30 minutes, and allowed to stir at room temperature for an additional 2.5 hours immediately after complete addition. The reacted mixture can be quenched by an addition of 50 mL of brine, and the organic solvent can be collected after separation. After removal of solvent, the crude product can be purified by silica-gel flash column chromatography via a hexane-ethyl acetate solvent system (e.g., gradient elution up to 45% volume ethyl acetate) to yield MTC-MPA (e.g., the amino-functionalized cyclic carbonate monomer 304) as a white fluffy solid. The crude product can be further purified by recrystallization. The solid can be dried and subsequently dissolved in 3 mL of dichloromethane and ethyl acetate respectively, followed by addition of 50 mL of diethyl ether. The crystals can be allowed to form at −20° C. for 1 day, and are subsequently obtained by washing the crystals with cold ether. A $^1$H NMR regarding the purified MTC-MPA (e.g., the amino-functionalized cyclic carbonate monomer 304) can observe the following results: δ7.29-6.68 (m, 5H, —$NC_6H_5$), 4.58-4.47 (s, 2H, —$OCOOCH_2$—), 4.45-4.34 (m, 2H, —$COOCH_2CH_2NR$—), 4.15-4.03 (m, 2H, —$OCOOCH_2$—), 3.72-3.62 (m, 2H, —$COOCH_2CH_2NR$—), 3.02-2.91 (m, 3H, —$NRCH_3$), 1.22-1.12 (m, 3H, —$CH_3$ on cyclic carbonate).

In a glove-box, 0.222 g (e.g., 0.022 mmol) of 10 kiloDa mPEG-OH initiator, 0.376 g (e.g., 1 mmol) of MTC-PPB (e.g., the cyclic carbonate monomer 206), and 0.293 g (e.g., 1 mmol) of MTC-MPA (e.g., the amino-functionalized cyclic carbonate monomer 304) can be charged in a 20 milliliter (mL) glass vial equipped with a stir bar. Dichloromethane can be added, and the monomer concentration can be adjusted to 2 M. Once the monomers are completely dissolved, 8.3 μL (e.g., 0.06 mmol) of DBU can be added to initiate the polymerization. After about 3.5 hours of stirring at room temperature, the reaction can be quenched with 30 milligrams (mg) of benzoic acid. Subsequently, the intermediate PEG-[P(MTC-PPBA)-co-P(MTC-MPA)] (e.g., the second intermediate 306) can be purified via precipitation twice in cold diethyl ether, and can be dried on a vacuum line until a constant weight was achieved. A proton nuclear magnetic resonance (e.g., $^1$H NMR) regarding the purified PEG-[P(MTC-PPBA)-co-P(MTC-MPA)] (e.g., the second intermediate polymer 306) can observe the following results: δ7.81-6.64 (m, 85H, —$C_6H_4B$= and —$NC_6H_5$), 5.24-5.05 (m, 20H, —$CH_2C_6H_4$—), 4.42-4.18 (m, 112H, —$OCOOCH_2$- & —$COOC_2H_4NR$—), 3.85-3.42 (m, 908H, —$OCH_2CH_2$— of 10 kiloDa mPEG), 3.35 (s, 3H, $CH_3$ of mPEG), 3.05-2.89 (m, 27H, —$NRCH_3$), 1.40-1.29 (m, 120H, 4×$CH_3$ on the protecting group), 1.28-1.14 (m, 57H, —$CH_3$on the polymer backbone). Additionally, the purified PEG-[P(MTC-PPBA)-co-P(MTC-MPA)] (e.g., the second intermediate polymer 306) can have a molecular weight of 12.5 kiloDa and/or a PDI of 1.16.

The protected PEG-[P(MTC-PPBA)-co-P(MTC-MPA)] (e.g., the second polymer intermediate 306) can then be deprotected by dissolving in 14 mL of methanol and THF (e.g., in a 1:1 ratio) and 10 equivalents (e.g., with respect to moles of protected phenylboronic pinacol pendant groups) of benzene-1,4-diboronic acid, and DOWEX® 50W-X2 acidic resins can be added to a 50 mL flask containing the protected PEG-[P(MTC-PPBA)-co-P(MTC-MPA)] polymer. The flask can subsequently be heated to 50° C. with overnight stirring. The solvents can be removed under vacuum and the deprotected polymer can be dissolved in 10 mL of isopropanol and acetonitrile (e.g., in a ratio of 1:1) and placed within a dialysis bag of 1000 molecular weight cut-off. Dialysis can be carried out for the next 2 days at room temperature using 1:1 isopropanol and acetonitrile. Finally, the solvents can be removed and the second polymer carrier 106 can be lyophilized to obtain an off-white polymer. A $^1$H NMR regarding the second polymer carrier 106 can observe the following results: δ8.13-6.58 (m, 99H, —$B(OH)_2$, —$C_6H_4B$= and —$NC_6H_5$), 5.20-5.03 (m, 18H, —$CH_2C_6H_4$—), 4.38-4.09 (m, 108H, —$OCOOCH_2$— & —$COOC_2H_4NR$—), 3.73-3.32 (m, 908H, —$OCH_2CH_2$— of 10 kiloDa mPEG), 3.24 (s, 3H, $CH_3$ of mPEG-), 2.86-2.78 (m, 27H, —$NRCH_3$), 1.32-0.97 (m, 54H, —$CH_3$ on the polymer backbone).

Therefore, the second polymer carrier 106 can be synthesized in similar fashion as the first polymer carrier 100, with the addition of equal equivalent of MTC-MPA monomer during polymerization process. The MTC-PPB had a DP of 10, whereas the DP of MTC-MPA was found to be 9. The DP of MTC-PPB was calculated from the methylene protons that was located between 5.30-5.01 ppm, whereas DP of MTC-MPA was derived from the methylene group located on the tertiary aniline between 3.05-2.85 ppm. The protected PEG-[P(MTC-PPBA)-co-P(MTC-MPA)] also had a narrow molecular weight distribution of 1.22. $^1$H NMR analysis depicts the presence of signal peak at 2.95 ppm (before deprotection) and 2.7 ppm (after deprotection), which correlates with the methyl protons on the aniline derivative moiety, indicating successful deprotection. The DP of MTC-PPB experienced a slight reduction from 10 to 9 (e.g., calculated from the methylene groups of phenylboronic acid at 5.25-5.05 ppm). The DP of aniline stayed constant at 9 (e.g., with methyl groups on the tertiary amine at 2.81-2.75 ppm).

Figure 4:
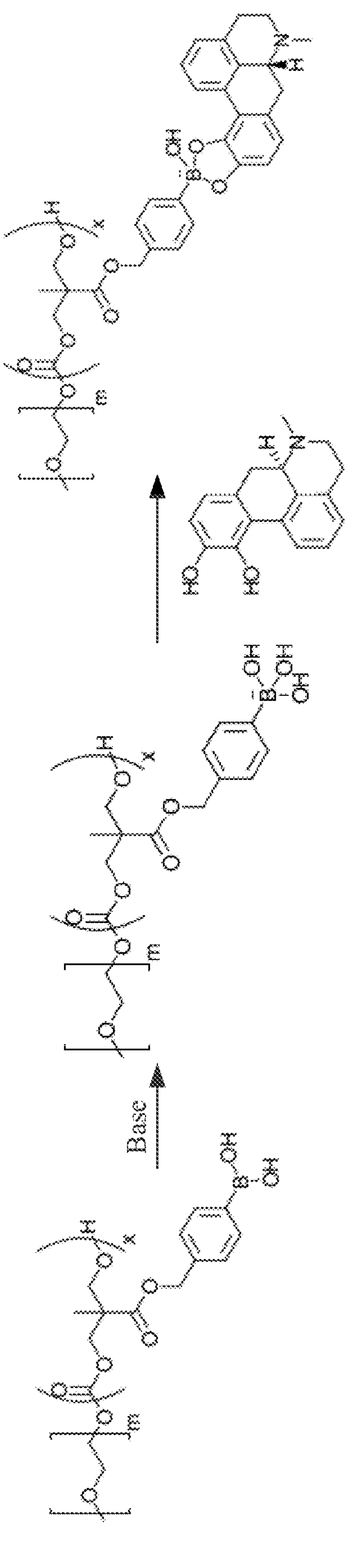
FIG. 4 illustrates a diagram of an example, non-limiting conjugation scheme to facilitate conjugating a molecular cargo with the first polymer that can facilitate transportation of the molecular cargo across the BBB in accordance with one or more embodiments described herein.

FIG. 4 illustrates a diagram of an example, non-limiting first conjugation scheme 400 that can facilitate conjugating one or more molecular cargos 402 with the first polymer carrier 100 in accordance with one or more embodiments described herein. Repetitive description of like elements employed in other embodiments described herein is omitted for sake of brevity. As shown in FIG. 4, one or more molecular cargos 402 can be complexed directly to the boronic acid structure of the first polymercarrier 100 in the presence of a base to form a first loaded polymer 404. Also shown in FIG. 4, "m" can be an integer greater than or equal to 45 and less than or equal to 454, and/or "x" can be an integer greater than or equal to 2 and less than or equal to 100.

The one or more molecular cargos 402 can be chemical compounds comprising a catechol moiety. Example molecular cargos 402 can include, but are not limited to: AMP, a chemical compound comprising 1,2-diol, a combination thereof, and/or the like. For instance, FIG. 4 depicts the conjugation of AMP to the first polymer carrier 100. The one or more molecular cargos 402 can conjugate to the first polymercarrier 100 in the presence of, for example, a molar ratio of base to boronic acid greater than or equal to 0.1:1 and less than or equal to 1:1. Example bases that can facilitate the conjugation of the first conjugation scheme 400 can include, but are not limited to: trimethylamine ("TEA"), 4-dimethylaminopyridine ("DMAP"), N,N-diisopropylethylamine ("DIEA"), pyridine, a combination thereof, and/or the like.

As shown in FIG. 4, the first conjugation scheme 400 can comprise forming a dynamic covalent boronate ester bond between the boronic acid structure of the first polymer carrier 100 and the catechol moiety of the one or more molecular cargos 402. The boronate ester bond can be a reversible covalent bond that is acidity-sensitive. The boronate ester bond of the first loaded polymer 404 can be formed near the pKa value of the boronic acid structure, and can be reversible under acidic conditions (e.g., conditions exhibiting a pH greater than or equal to 4.0 and less than or equal to 6.8). In one or more embodiments, the introduction of electron withdrawing groups and/or the addition of nitrogen center adjacent to the boron can lower the pKa to facilitate formation of the boronate ester bond. Thus, the first conjugation scheme 400 can facilitate a molecular encapsulation of the one or more molecular cargos 402 by the formation of dynamic (e.g., acidity-sensitive) covalent boronate ester bond between the boronic acid structure of the first polymercarrier 100 and the catechol moiety of the molecular cargo 402.

Figure 5:
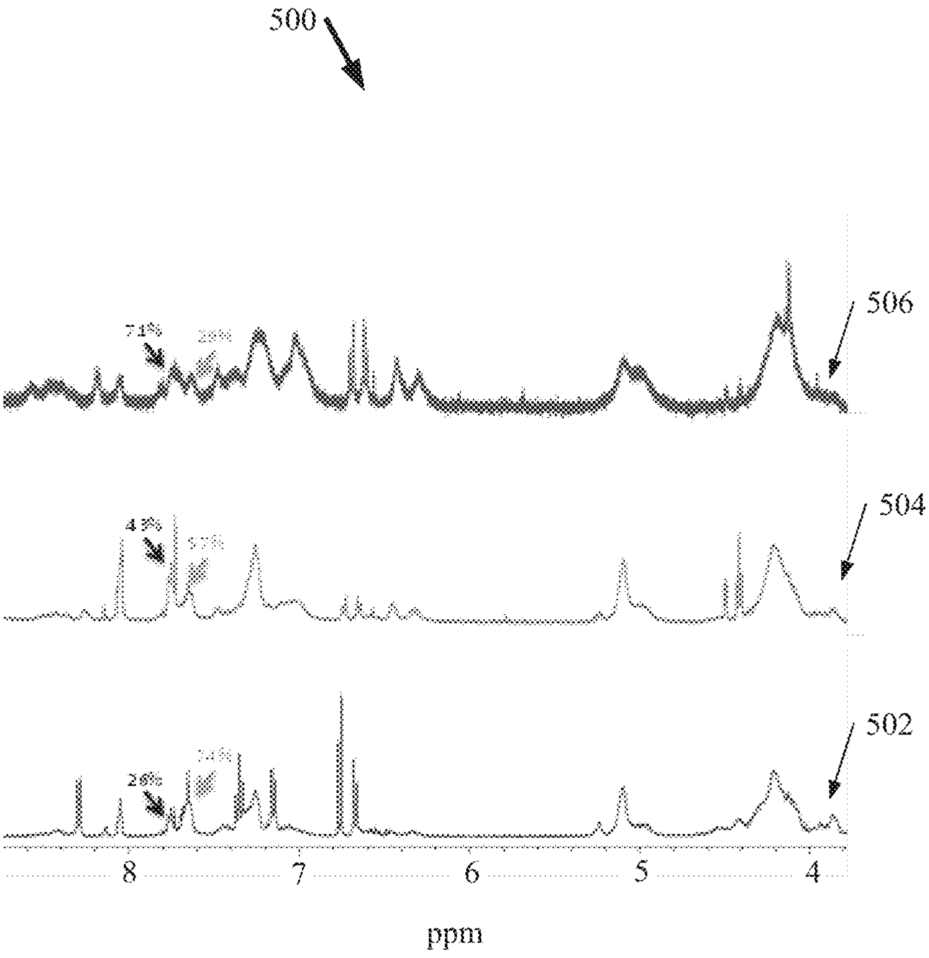
FIG. 5 illustrates a diagram of an example non-limiting graph that can demonstrate the efficacy of the conjugation of a molecular cargo with the first polymer that can facilitate transportation of the molecular cargo across the BBB in accordance with one or more embodiments described herein.

FIG. 5 illustrates a diagram of an example, non-limiting $^1H$ NMR spectra 500 of an AMP/first polymercarrier 100 conjugate (e.g., the first loaded polymer 404, wherein the molecular cargo 402 can be AMP and the first polycarbonate structure 104 can be a phenylboronic acid-functionalized polycarbonate) in accordance with one or more embodiments described herein. Repetitive description of like elements employed in other embodiments described herein is omitted for sake of brevity. With regards to FIG. 5, the AMP/first polymer carrier 100 conjugate can be formed in accordance with the first conjugation scheme 400 using three different bases.

The loading content of AMP was determined through high performance liquid chromatography ("HPLC"). AMP-loaded polymers (e.g., 1 mg) (e.g., the first loaded polymer 404) was dissolved in 1 mL of acidified methanol and filtered with a 0.2 μm syringe filter for HPLC analysis (e.g., using a Water 2690 separation module, a Waters 996 photodiode array detector, and a Waters XBridge $C_8$ 46×150 mm). The mobile phase was methanol, elution rate was set at 1 mL/min and detection wavelength at 274 nm.

The first line 502, depicts the formation of the AMP/first polymercarrier 100 conjugate in accordance with the first conjugation scheme 400, wherein pyridine is the base organocatalyst. For example, a 0.1 molar ratio of pyridine to boronic acid was used to conduct the conjugation characterized by the first line 502. The second line 504, depicts the formation of the AMP/first polymercarrier 100 conjugate in accordance with the first conjugation scheme 400, wherein DIEA is the base organocatalyst. For example, a 0.1 molar ratio of DIEA to boronic acid was used to conduct the conjugation characterized by the second line 504. The third line 506, depicts the formation of the AMP/first polymercarrier 100 conjugate in accordance with the first conjugation scheme 400, wherein DMAP is the base organocatalyst. For example, a 0.1 molar ratio of DMAP to boronic acid was used to conduct the conjugation characterized by the third line 506.

The arrows shown in the $^1H$ NMR spectra 500 can indicate the proton shifts corresponding to the conjugates, and the percentages can indicate relative ratios of designated peaks. As shown in FIG. 5, while strong bases such as DMAP and DIEA led to polymer degradation and lower molecular cargo 402 conjugation, pyridine offered a relatively high conjugation degree (74%) without polymer degradation.

Figure 6:
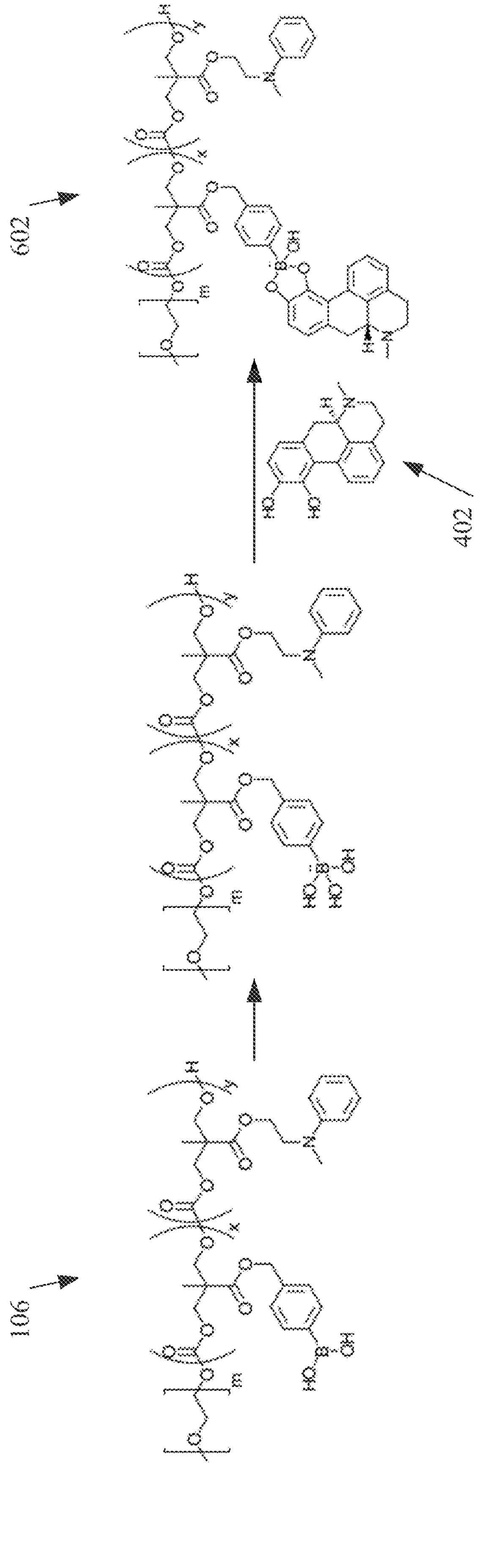
FIG. 6 illustrates a diagram of an example, non-limiting conjugation scheme to facilitate conjugating a molecular cargo with the second polymer that can facilitate transportation of the molecular cargo across the BBB in accordance with one or more embodiments described herein.

FIG. 6 illustrates a diagram of an example, non-limiting second conjugation scheme 600 that can facilitate conjugating the one or more molecular cargos 402 with the second polymer carrier 106 in accordance with one or more embodiments described herein. Repetitive description of like elements employed in other embodiments described herein is omitted for sake of brevity. As shown in FIG. 6, the one or more molecular cargos 402 can be complexed directly to the boronic acid structure of the second polymer carrier 106 to form a second loaded polymer 602. Also shown in FIG. 6, "m" can be an integer greater than or equal to 45 and less than or equal to 454, "x" can be an integer greater than or equal to 2 and less than or equal to 50, and/or "y" can be an integer greater than or equal to 2 and less than or equal to 50.

As described with regards to the first conjugation scheme 400, the one or more molecular cargos 402 can be chemical compounds comprising a catechol moiety. Example molecular cargos 402 can include, but are not limited to: AMP, a chemical compound comprising 1,2-diol, a combination thereof, and/or the like. For instance, FIG. 6 depicts the conjugation of AMP to the second polymer carrier 106.

As shown in FIG. 6, the second conjugation scheme 600 can comprise forming a dynamic covalent boronate ester bond between the boronic acid structure of the second polymer carrier 106 and the catechol moiety of the one or more molecular cargos 402. The boronate ester bond can be a reversible covalent bond that is acidity-sensitive. The boronate ester bond of the second loaded polymer 602 can be formed near the pKa value of the boronic acid structure, and can be reversible under acidic conditions (e.g., conditions exhibiting a pH greater than or equal to 4.0 and less than or equal to 6.8). In one or more embodiments, the introduction of electron withdrawing groups and/or the addition of nitrogen center adjacent to the boron can lower the pKa to facilitate formation of the boronate ester bond.

Additionally, the amino group comprised within the second polycarbonate structure 108 of the second polymer carrier 106 can serve as a catalyst to accelerate molecular cargo 402 conjugation. For example, the amino-functionalized polycarbonate of the second polymer carrier 106 can comprise a tertiary amine that can serve as a catalyst to the second conjugation scheme 600. For instance, the second polycarbonate structure 108 can comprise an aniline-functionalized polycarbonate with a tertiary amine, as depicted in FIG. 6. Advantageously, the incorporation of the amino functional group into the molecular backbone of the second polymer carrier 106 (e.g., via the second polycarbonate structure 108) can alleviate the need for a base organocatalyst to facilitate the second conjugation scheme 600, wherein the incorporated amino functional group can reduce the pKa value of the boronic acid functional group and enable conjugation of the one or more molecular cargos 402 under neutral conditions. Thus, the second conjugation scheme 600 can facilitate a molecular encapsulation of the one or more molecular cargos 402 by the formation of dynamic (e.g., acidity-sensitive) covalent boronate ester bond between the boronic acid structure of the second polymer carrier 106 and the catechol moiety of the molecular cargo 402, wherein the amino functional group of the second polymer carrier 106 can serve as an integrated catalyst to the formation of the dynamic covalent boronate ester bond.

Figure 7:
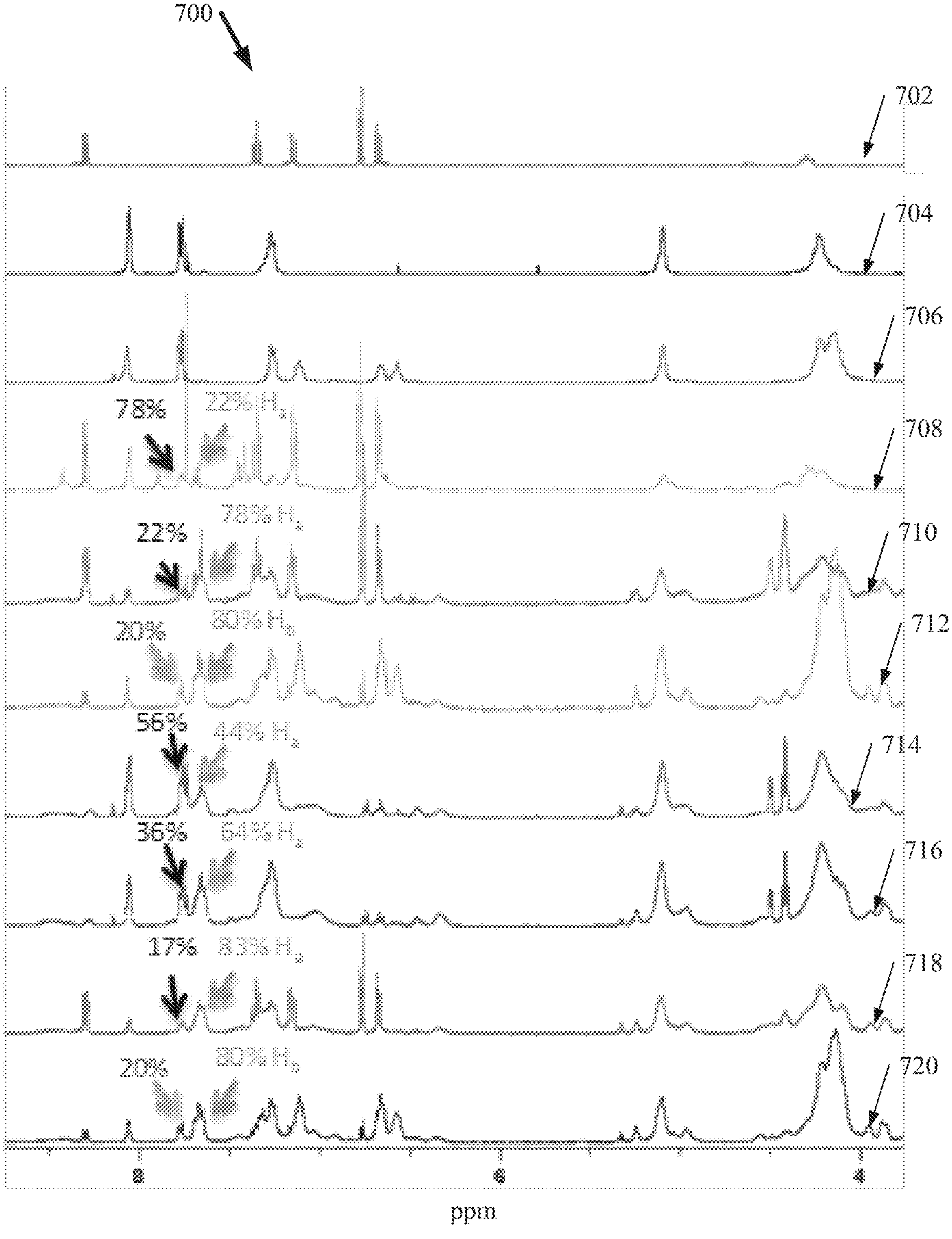
FIG. 7 illustrates a diagram of an example, non-limiting graph that can demonstrate the efficacy of the conjugation of a molecular cargo with the first polymer or the second polymer, which can facilitate transportation of the molecular cargo across the BBB in accordance with one or more embodiments described herein.

FIG. 7 illustrates a diagram of an example, non-limiting $^1H$ NMR spectra 700 of AMP, the first polymer carrier 100, the second polymer carrier 106, the first loaded polymer 404 under various conjugation conditions, and/or the second loaded polymer 602 under various conjugation conditions in accordance with one or more embodiments described herein. Repetitive description of like elements employed in other embodiments described herein is omitted for sake of brevity. The arrows shown in the $^1H$ NMR spectra 700 can indicate the proton shifts corresponding to the conjugates, and the percentages can indicate relative ratios of designated peaks.

The loading content of AMP was determined through high performance liquid chromatography ("HPLC"). AMP-loaded polymers (e.g., 1 mg) (e.g., the first loaded polymer 404) was dissolved in 1 mL of acidified methanol and filtered with a 0.2 μm syringe filter for HPLC analysis (e.g., using a Water 2690 separation module, a Waters 996 photodiode array detector, and a Waters XBridge $C_8$ 46×150 mm). The mobile phase was methanol, elution rate was set at 1 mL/min and detection wavelength at 274 nm.

The first line 702 of FIG. 7 can represent the $^1$H NMR spectra of AMP. The second line 704 of FIG. 7 can represent the $^1$H NMR spectra of the first polymercarrier 100 having the exemplary structure depicted in FIG. 1A. The third line 706 of FIG. 7 can represent the $^1$H NMR spectra of the second polymer carrier 106 having the exemplary structure depicted in FIG. 1B. The fourth line 708 of FIG. 7 can represent the $^1$H NMR spectra of the first loaded polymer 404 having the exemplary structure depicted in FIG. 4 and formed with a molar ratio of AMP to first polymercarrier 100 equal to 3:1. The fifth line 710 of FIG. 7 can represent the $^1$H NMR spectra of the first loaded polymer 404 having the exemplary structure depicted in FIG. 4 and formed in the presence of TEA for five minutes, wherein with a molar ratio of AMP to first polymercarrier 100 was 3:1 and a molar ratio of TEA to boronic acid was 0.1:1. The sixth line 712 of FIG. 7 can represent the $^1$H NMR spectra of the second loaded polymer 602 having the exemplary structure depicted in FIG. 6 and formed in five minutes with a molar ratio of AMP to second polymer carrier 106 was equal to 3:1. The seventh line 714 of FIG. 7 can represent the $^1$H NMR spectra of the first loaded polymer 404 having the exemplary structure depicted in FIG. 4 and formed in the presence of TEA for thirty minutes, wherein with a molar ratio of AMP to first polymercarrier 100 was 1.5:1 and a molar ratio of TEA to boronic acid was 0.1:1. The eighth line 716 of FIG. 7 can represent the $^1$H NMR spectra of the first loaded polymer 404 having the exemplary structure depicted in FIG. 4 and formed in the presence of TEA for thirty minutes, wherein with a molar ratio of AMP to first polymercarrier 100 was 2:1 and a molar ratio of TEA to boronic acid was 0.1:1. The ninth line 718 of FIG. 7 can represent the $^1$H NMR spectra of the first loaded polymer 404 having the exemplary structure depicted in FIG. 4 and formed in the presence of TEA for thirty minutes, wherein with a molar ratio of AMP to first polymercarrier 100 was 3:1 and a molar ratio of TEA to boronic acid was 0.1:1. The tenth line 720 of FIG. 7 can represent the $^1$H NMR spectra of the second loaded polymer 602 having the exemplary structure depicted in FIG. 6 and formed in thirty minutes with a molar ratio of AMP to second polymer carrier 106 equal to 3:1.

As shown in FIG. 7, the $^1$H NMR spectra of AMP, the first polymercarrier 100 with the exemplary structure depicted in FIG. 1A, and the first loaded polymer 404 with the exemplary structure depicted in FIG. 4 were analyzed. Appearance of a new upfield proton peak $H_a$ at 7.68-7.55 ppm adjacent to the peak at 7.80-7.75 ppm can indicate the condensation of the para-substituted phenylboronic acid pendant groups of the polymer with the catecholic moiety of AMP, resulting in shielding of the aromatic proton. The ratio between the area under the peaks of 7.68-7.55 (conjugated) and 7.80-7.75 (non-conjugated) ppm were compared to attain the degree of conjugation.

Also shown in FIG. 7, covalent boronate ester interactions with regards to the first polymercarrier 100 can be enhanced by organocatalytic activation of phenylboronic acid. The conjugation degree of AMP for the first polymercarrier 100 (e.g., having the exemplary structure depicted in FIG. 1A) was 85% over 24 hours and 22% over 5 min (as shown by the third line 706), respectively. In contrast, the utilization of 0.1% TEA with the first polymer carrier 100 and AMP gave rise to 78% conjugation degree (e.g., with a molar ratio of initial AMP to first polymercarrier 100 equal to 3:1) after 5 minutes (e.g., as depicted by the fifth line 710). Furthermore, the first polymercarrier 100 was mixed with AMP for 30 minutes at varying AMP concentrations that ranged between 1.5 to 3.0 equivalents together with 0.1% of TEA, where it was ascertained that the greatest amount of conjugation (83%) was with 3 mole equivalents of AMP (e.g., as depicted in FIG. 7). However, use of TEA in 5 minute or 30 minute reactions led to polymer degradation as shown from the sharp monomer peaks appearing in the region of 4.5-4.0 ppm.

Further shown in FIG. 7, the introduction of tertiary amine groups to the polycarbonate block of the second polymer carrier 106 (e.g., having the exemplary structure depicted in FIG. 1B) resulted in 80% AMP conjugation degree in either 5 minute or 30 minute reactions without causing polymer degradation, demonstrating that the tertiary amine groups in the second polymer carrier 106 served as a catalyst for the reaction.

Moreover, the first loaded polymers 404 and/or the second loaded polymers 602 can self-assemble into nanoparticles with sizes slightly larger than the first polymercarrier 100 and/or the second polymer carrier 106 but still around 100 nm, well below the 300 nm threshold for crossing the BBB. Also, the loaded nanoparticles can have monodispersed distribution with low PDI values. For example, Table 1, presented below, depicts one or more size characteristics of: the first polymercarrier 100 having the exemplary structure depicted in FIG. 1A, the first loaded polymer 404 having the exemplary structure depicted in FIG. 4, the second polymer carrier 106 having the exemplary structure depicted in FIG. 1B, and/or the second loaded polymer 602 having the exemplary structure depicted in FIG. 6.

TABLE 1

| | $M_n$ ($M_n/M_w$) | Particle Size (nm) | PDI | AMP loading (wt %) |
|---|---|---|---|---|
| First Polymer Carrier 100 | 13,000 (1.16) | 54 ± 3 | 0.11 ± 0.01 | — |
| First Loaded Polymer 404 | — | 104 ± 6 | 0.15 ± 0.01 | 21.4 ± 2.3 |
| Second Polymer Carrier 106 | 12,000 (1.22) | 71 ± 3 | 0.13 ± 0.01 | — |
| Second Loaded Polymer 602 | — | 92 ± 5 | 0.18 ± 0.01 | 24.1 ± 2.8 |

Wherein "$M_n$" can represent the number average molar mass, and "$M_w$" can represent the mass average molar mass. Particle size of the polymeric nanoparticles and the AMP-loaded nanoparticles was measured by dynamic light scattering ("DLS") using the Zetasizer Nano ZS with a 633 nm He-Ne laser.

Figure 8:
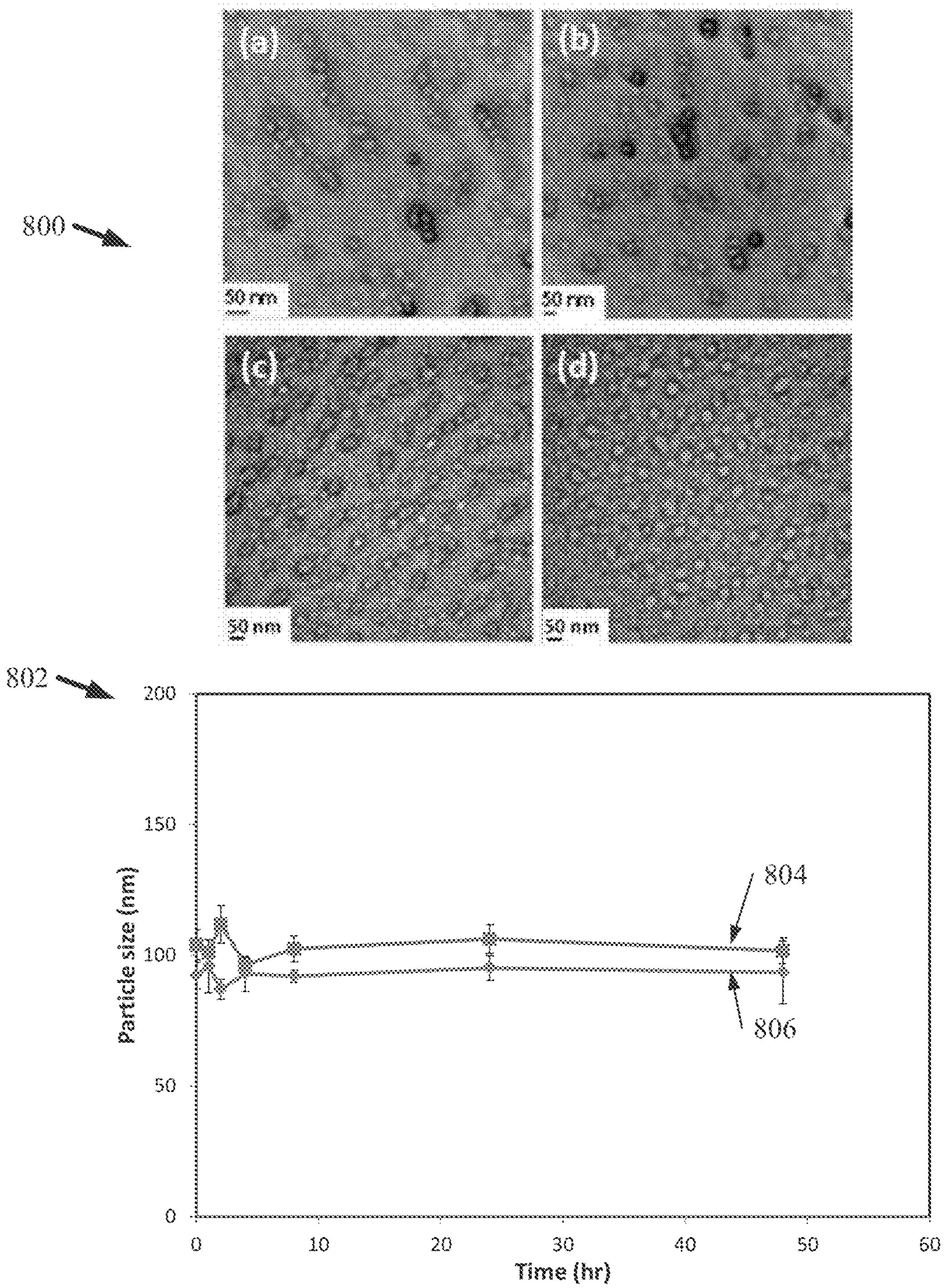
FIG. 8 illustrates a diagram of example, non-limiting photos and/or a chart regarding exemplary particle sizes of the first polymer and/or the second polymer loaded with a molecular cargo in accordance with one or more embodiments described herein.

FIG. 8 illustrates a diagram of example, non-limiting TEM images 800 and a graph 802 regarding the first polymercarrier 100 having the exemplary structure depicted in FIG. 1A, the first loaded polymer 404 having the exemplary structure depicted in FIG. 4, the second polymer carrier 106 having the exemplary structure depicted in FIG. 1B, and/or the second loaded polymer 602 having the exemplary structure depicted in FIG. 6 in accordance with one or more embodiments described herein. Repetitive description of like elements employed in other embodiments described herein is omitted for sake of brevity.

Morphology of the nanoparticles was visualized using a FEI Tecnai $G^2$ F20 electron microscope. The nanoparticle suspension (e.g., 5 μL) was placed onto 200 mesh formvar/carbon copper grid for 1 minute before the excess suspension was removed, followed by addition of 5 μL of 0.25 mass/volume ("w/v") phosphotungstic acid. After 1 minute, the excess solution can be removed, and copper grid was left at room temperature to dry prior to observation under TEM.

The TEM image 800 labelled "(a)" in FIG. 8 regards the first polymercarrier 100 having the exemplary structure depicted in FIG. 1A. The TEM image 800 labelled "(b)" in FIG. 8 regards the first loaded polymer 404 having the exemplary structure depicted in FIG. 4. The TEM image 800 labelled "(c)" in FIG. 8 regards the second polymer carrier 106 having the exemplary structure depicted in FIG. 1B. The TEM image 800 labelled "(d)" in FIG. 8 regards the second loaded polymer 602 having the exemplary structure depicted in FIG. 6. As shown in the TEM images 800 of FIG. 8, the nanoparticles (e.g., the AMP loaded nanoparticles and/or the un-loaded polymeric nanoparticles) described herein have spherical particles with sizes that are in agreement with those obtained through DLS.

Further, graph 802 shows that the sizes of both conjugates can be stable and remain similar throughout a 48 hour incubation in phosphate-buffered saline ("PBS") containing 10% fetal bovine serum ("FBS"). The first line 804 of graph 802 can represent the first loaded polymer 404 having the exemplary structure depicted in FIG. 4. The second line 806 of graph 802 can represent the second loaded polymer 602 having the exemplary structure depicted in FIG. 6. Graph 802 can show the potential of these AMP conjugated nanoparticles (e.g., first loaded polymer 404 and/or second loaded polymer 602) to be used in in vivo applications.

Figure 9:
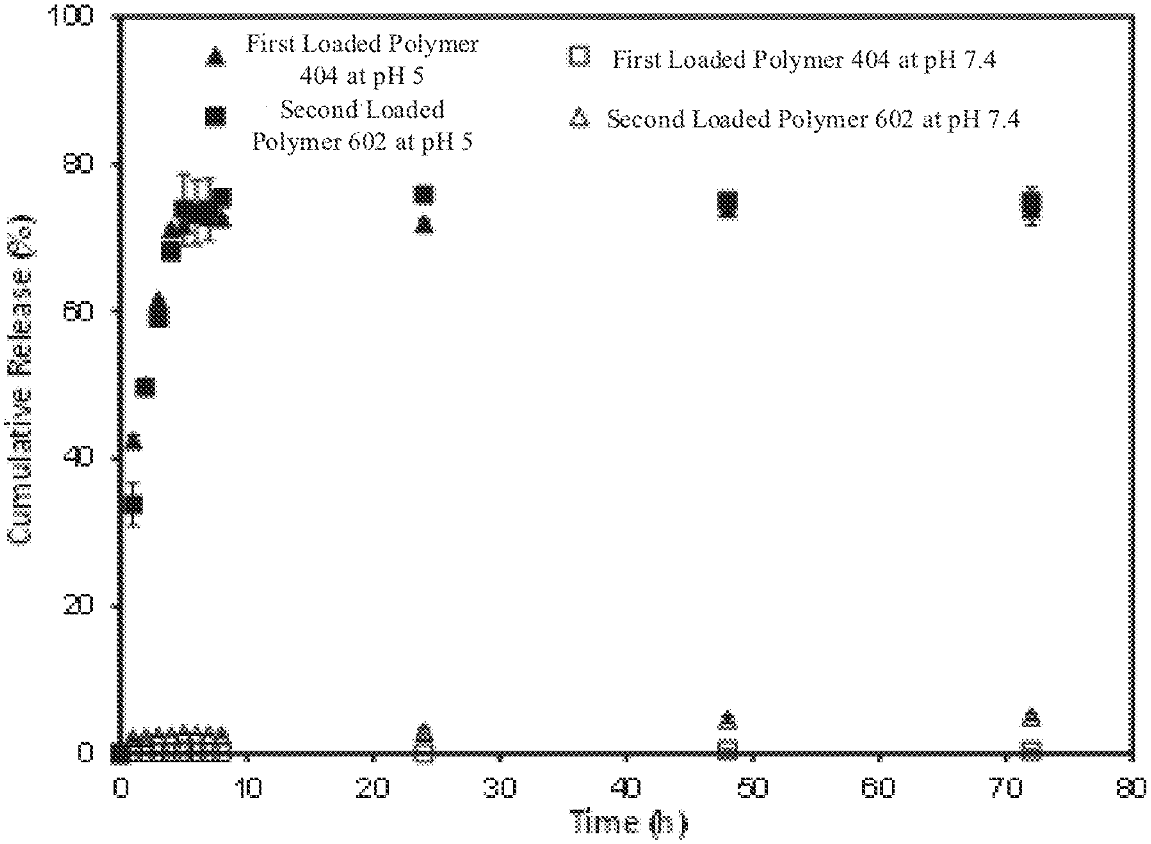
FIG. 9 illustrates a diagram of example, non-limiting graph that can demonstrate one or more characteristics of a biologically triggered release of molecular cargo that the first polymer and/or the second polymer can exhibit in accordance with one or more embodiments described herein.

FIG. 9 illustrates a diagram of an example, non-limiting graph 900 that can biologically triggered release of the molecular cargo 402 that can be facilitated by the dynamic covalent boronate ester bond of the first loaded polymer 404 and/or the second loaded polymer 602 in accordance with one or more embodiments described herein. Repetitive description of like elements employed in other embodiments described herein is omitted for sake of brevity. Graph 900 can depict in vitro release profiles of the first loaded polymer 404 having the exemplary structure depicted in FIG. 4 and/or the second loaded polymer 602 having the exemplary structure depicted in FIG. 6 at a pH of 5 (e.g., in 150 millimolar (mM) of sodium acetate buffer) and a pH of 7.4 (e.g., in 150 mM of PBS) at 37° C.

For example, to develop the data depicted in graph 900, a concentration of 1 mg/mL of AMP-loaded nanoparticles (e.g., first loaded polymer 404 having the exemplary structure depicted in FIG. 4 and/or the second loaded polymer 602 having the exemplary structure depicted in FIG. 6) was prepared with either 150 mM PBS (e.g., pH 7.4) or 150 mM sodium acetate buffer (e.g., pH 5.0). The suspended nanoparticles (e.g., 3 mL) were placed in a 1000 Da cut off dialysis membrane and then immersed into 30 mL of sodium acetate buffer (e.g., pH 5) or PBS (e.g., pH 7.4). At regular time intervals, 1 mL of the buffer was removed and replaced with fresh buffer. HPLC was used to determine the amount of AMP released.

Premature release can be a major issue for conventional chemical compound delivery systems as it can result in harmful side effects and/or low efficacy. The release profiles of AMP from the first loaded polymer 404 and/or the second loaded polymer 602 are presented in graph 900 under two different pH conditions (e.g., pH 5 and pH 7.4) for 72 hours at 37° C. At pH 7.4, no significant release of AMP can be observed from both formulations. However, when the pH was changed to acidic (e.g., pH 5, in endolysosomes), significant release of AMP can be observed, and there can be about 75% of AMP molecules released from the nanoparticles in 8 hours. The results depicted in graph 900 can demonstrate that AMP can be released from the nanoparticles described herein in acidic endolysosomes for its biological functions.

Figure 10:
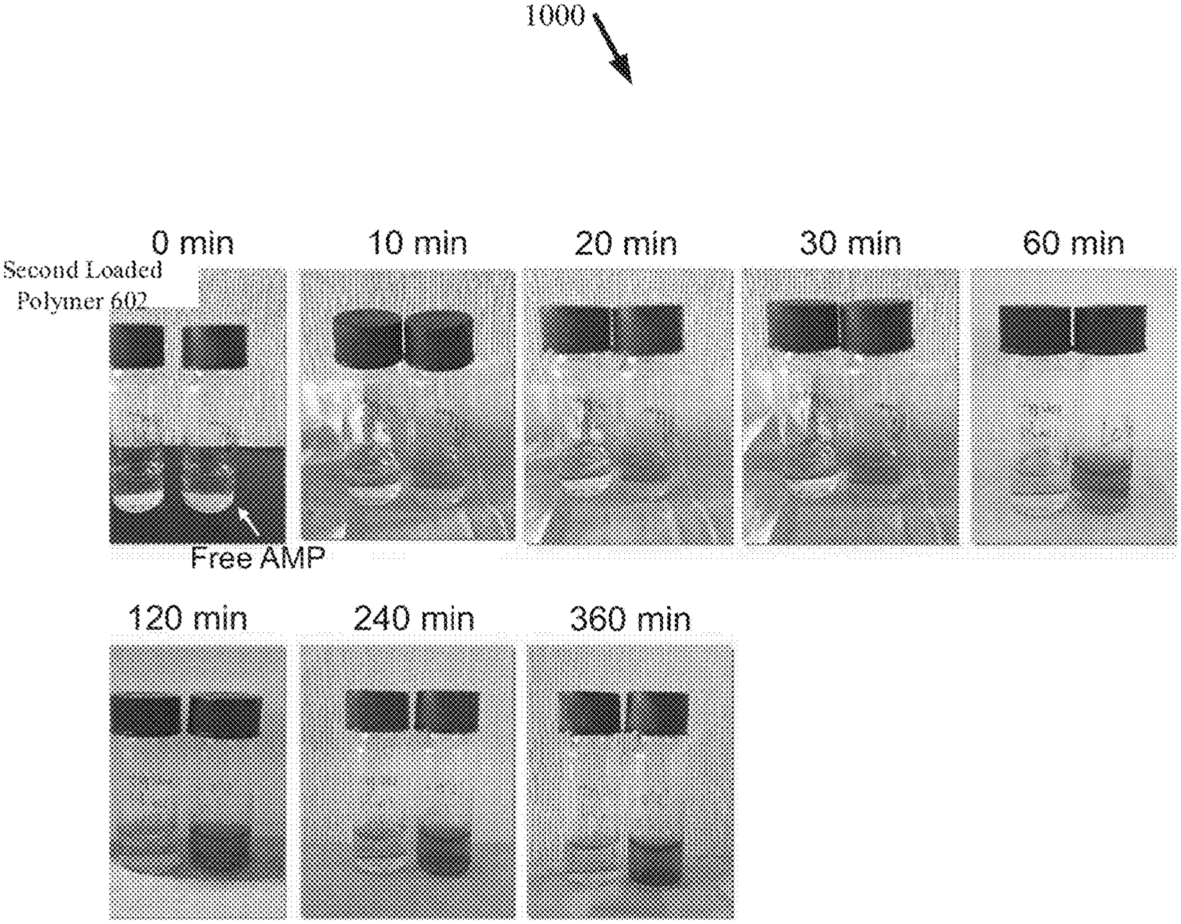
FIG. 10 illustrates a diagram of example, non-limiting photos that can demonstrate a molecular stability of the second polymer loaded with a molecular cargo in one or more environments that can facilitate oxidation of the otherwise isolated molecular cargo in accordance with one or more embodiments described herein.

FIG. 10 illustrates a diagram of example, non-limiting photos 1000 of a first solution of free AMP and a second solution of the second loaded polymer 602 having the exemplary structure depicted in FIG. 6 (e.g., conjugated with AMP) in accordance with one or more embodiments described herein. Repetitive description of like elements employed in other embodiments described herein is omitted for sake of brevity. As shown in the photos 1000, the right vial contains free AMP dispersed in PBS, and the left vial contains of the second loaded polymer 602 having the exemplary structure depicted in FIG. 6 (e.g., conjugated with AMP) dispersed in PBS. The various photos 1000 can show the state of the two solutions over a 360 minute time period.

Both solutions begin colorless, wherein the solutions become discolored in response to oxidation. FIG. 10 exemplifies that the non-protected AMP can oxidize nearly immediately upon dissolution in PBS, while the second polymer carrier 106 can delay the onset of AMP oxidation (e.g., via a molecular encapsulation established by a dynamic covalent boronate ester bond) by 60 minutes and/or can significantly inhibit AMP oxidation and reduce oxidation degree.

AMP can undergo auto-oxidation in aqueous solution in the presence of air to form cytotoxic quinone and semiquinone derivatives. The oxidative products from AMP can cause necrosis and/or deoxyribonucleic acid ("DNA") fragmentation in neurons and glial C6 cells. Through the encapsulation of AMP into the nanoparticles (e.g., the first polymer carrier 100 and/or the second polymer carrier 106), oxidization of AMP can be significantly inhibited. Conventional encapsulation techniques can have an initial burst release of dopamine due to physical encapsulation of dopamine and diffusion of surface adhered dopamine. The premature release of dopamine can lead to oxidation into free radicals before reaching the brain. In contrast, loading molecular cargo 402 (e.g., AMP) through the reversible covalent bond of the first loaded polymer 404 and/or the second loaded polymer 602 can protect the molecular cargo 402 (e.g., AMP) while also mitigating an initial burst release.

Figure 11:
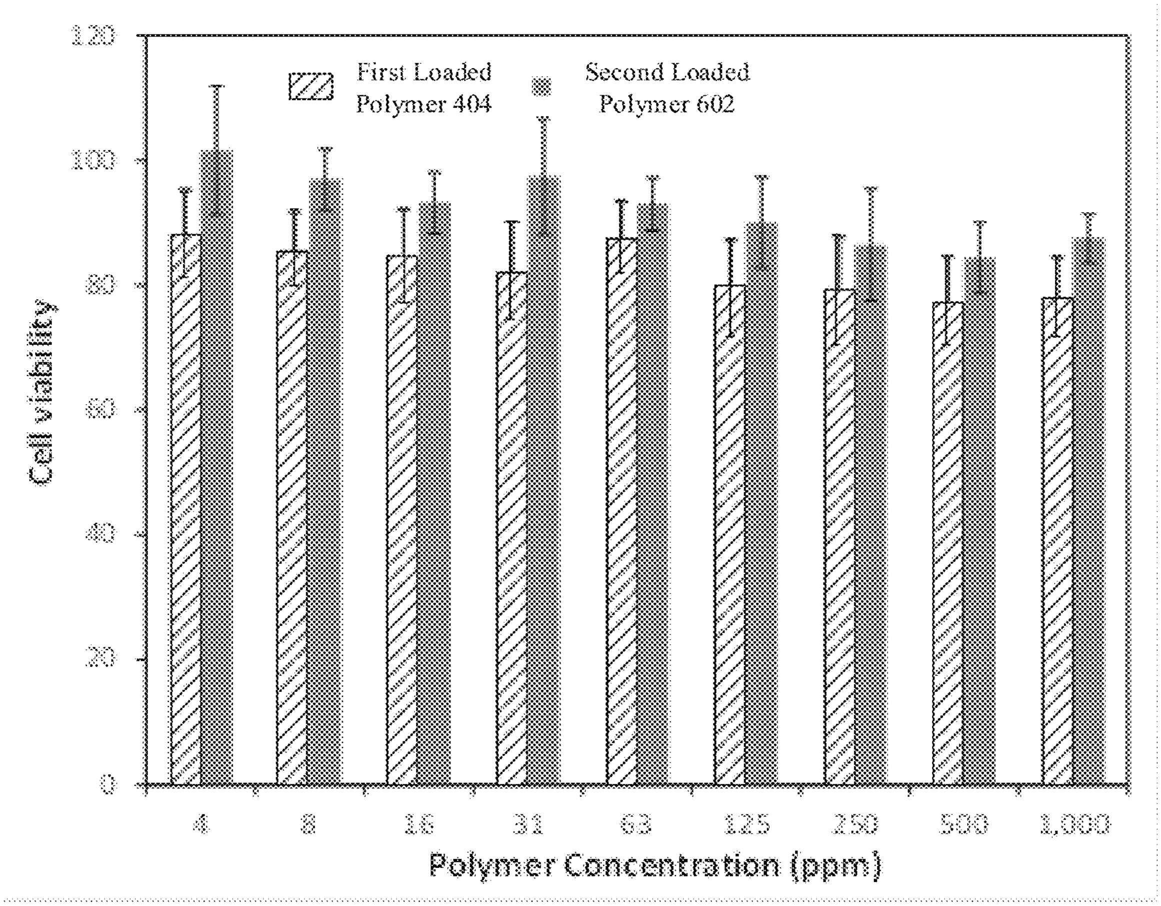
FIG. 11 illustrates a diagram of an example, non-limiting graph that can demonstrate cell viability in the presence of the first polymer and/or the second polymer in accordance with one or more embodiments described herein.

FIG. 11 illustrates a diagram of an example, non-limiting graph 1100 that can depict the viability of human embryonic kidney 293 ("HEK 293") cells after a 48 hour incubation with the first loaded polymer 404 having the exemplary structure depicted in FIG. 4 and the second loaded polymer 602 having the exemplary structure depicted in FIG. 6 in accordance with one or more embodiments described herein. Repetitive description of like elements employed in other embodiments described herein is omitted for sake of brevity.

As shown in FIG. 11, both loaded polymers (e.g., first loaded polymer 404 and/or second loaded polymer 602) can demonstrate no cytotoxicity in HEK 293 cell line up to a concentration of 1000 μg/mL with cell viability maintained at least more than 80% for all concentrations tested after the 48 hour incubation.

Figure 12:
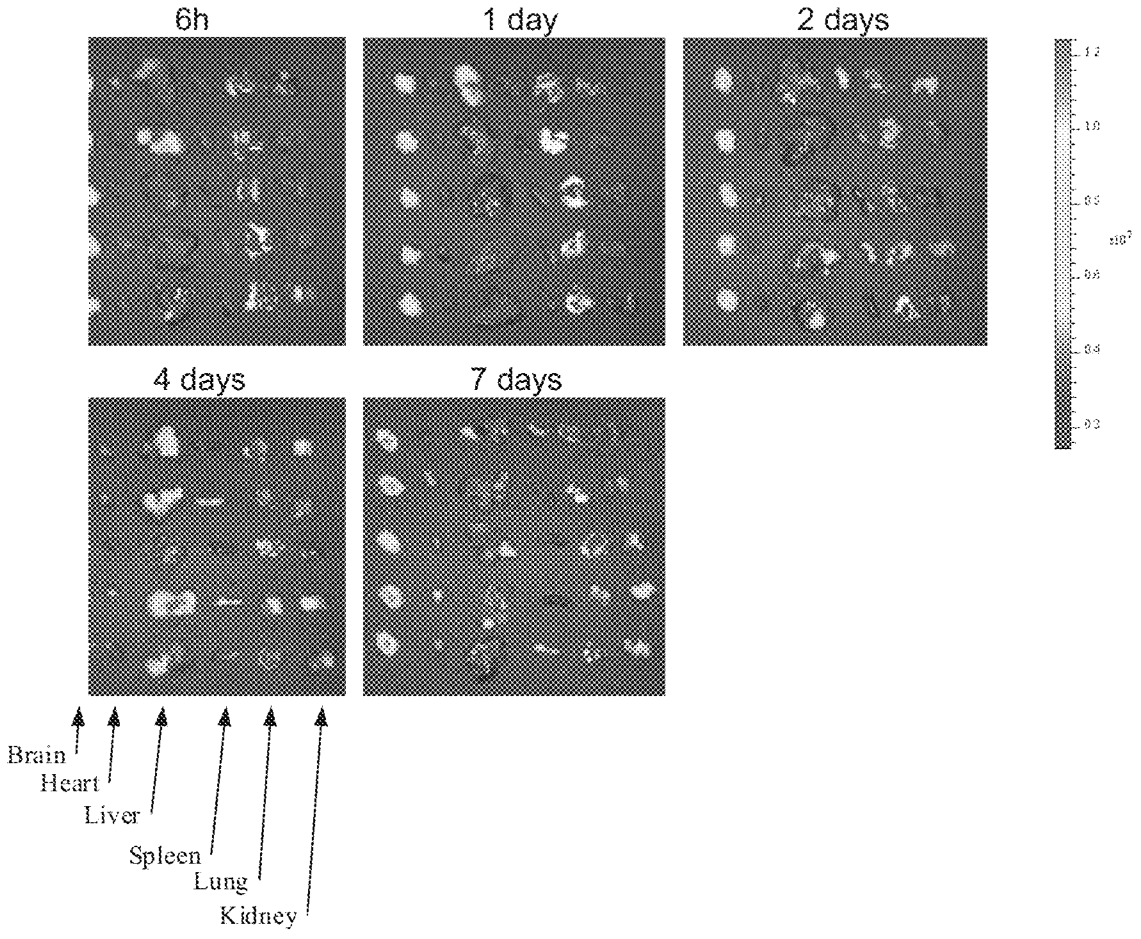
FIG. 12 illustrates a diagram of example, non-limiting slides that can depict the uptake of the second polymer with regards to various types of biological cells over a period of time in accordance with one or more embodiments described herein.

FIG. 12 illustrates a diagram of example, non-limiting biodistribution images 1200 of various organ tissues at different time points as specified after intranasal administration of $DilC_{18}(7)$ (1,1'-dioctadecyl-3,3,3',3'-tetramethylindotricarbocyanine iodide) ("DiR") and a conjugate of DiR and the second polymer carrier 106 in accordance with one or more embodiments described herein. Repetitive description of like elements employed in other embodiments described herein is omitted for sake of brevity. As shown in FIG. 12, each column of the biodistribution images 1200 can regard brain tissue, heart tissue, liver tissue, spleen tissue, lung tissue, and kidney tissue respectively.

To prepare the biodistribution images 1200, DiR, a near infrared fluorophore, was loaded into the second polymer carrier 106 having the exemplary structure depicted in FIG. 1B through a sonication/dialysis method. For example, 10 mg of the second polymer carrier 106 and 0.3 mg of DiR were dissolved in 2 mL of dimethyl sulfoxide ("DMSO") and added dropwise to 10 mL of de-ionized ("DI") water with sonication for 10 minutes. The mixture was dialyzed with DI water for 48 hours using a 1000 Da cut-off membrane, and water was changed at the third hour, the sixth hour, and the twenty-fourth hour. DiR loading level was determined by dissolving a known amount of lyophilized DiR-loaded nanoparticles in DMSO and measuring the absorbance using an ultraviolet-visible ("UV-VIS") spectrophotometer at 759 nm. Balb/c mice were treated with either 20 μl of DiR-loaded nanoparticles (e.g., 8 mg per kg of mouse body weight) or free DiR dissolved in DMSO-containing water (e.g., 0.1%) via intranasal administration. Organs were harvested and imaged at various time points depicted in FIG. 12 using the Xenogen IVIS 100 (e.g., with excitation at 710-760 nm and emission at 810-875 nm).

The size of the DiR-encapsulated second loaded polymer 602 nanoparticles can be 102±2 nm with a PDI of 0.12±0.02. Free DiR was dissolved in PBS with the aid of 1% DMSO and DiR-encapsulated second loaded polymer 602 nanoparticles dispersed in PBS were administrated into the mice through an intranasal route. The biodistribution of the nanoparticles was monitored through non-invasive near infrared fluorescence ("NIRF") imaging over 7 days. At each time point, organs were excised and imaged. After 6 hours post administration, DiR-encapsulated second loaded polymer 602 nanoparticles could be seen in the brain tissue, demonstrating that the nanoparticles crossed the BBB. Also, the accumulation of DiR was seen to increase with time in the brain over 7 days.

In various embodiments, molecular cargo 402 (e.g., AMP) can be conjugated to phenylboronic acid-containing amphiphilic polycarbonates to form a pH-sensitive boronate ester bond. The use of bases can accelerate the conjugation and increases conjugation degree. However, strong bases can also cause polymer degradation. The relatively weak base pyridine can mitigate polymer degradation and achieves high conjugation degree. In addition, the incorporation of amine groups (e.g., tertiary amine groups) into the phenylboronic acid-containing polycarbonate block can promote the formation of boronate ester bond between the molecular cargo 402 (e.g., AMP) and the polymer carrier (e.g., the first polymercarrier 100 and/or the second polymer carrier 106) without polymer degradation. The encapsulation of molecular cargo 402 (e.g., AMP) into the polymer carrier nanoparticles can inhibit oxidization, and intranasal administration of the loaded nanoparticles (e.g., the first loaded polymer 404 and/or the second loaded polymer 602) can transport the molecular cargo 402 (e.g., AMP) across the BBB. These loaded nanoparticles may be used for treatment of one or more neurodegenerative disorders, such as Parkinson's disease.

Figure 13:
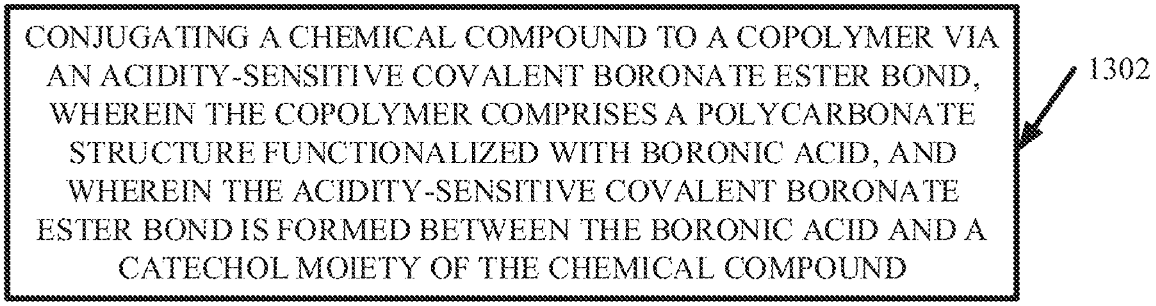
FIG. 13 illustrates a flow diagram of an example, non-limiting method that can facilitate conjugating one or more molecular cargos with the first polymer and/or the second polymer in accordance with one or more embodiments described herein.

FIG. 13 illustrates a flow diagram of an example, non-limiting method 1300 that can facilitate transporting one or more chemical compounds across the BBB in accordance with one or more embodiments described herein. Repetitive description of like elements employed in other embodiments described herein is omitted for sake of brevity.

At 1302, the method 1300 can comprise conjugating one or more chemical compound (e.g., one or more molecular cargos 402) to one or more copolymers (e.g., one or more first polymer carriers 100 and/or one or more second polymer carriers 106) via an acidity-sensitive (e.g., a pH-sensitive) covalent boronate ester bond. The one or more copolymers can comprise a polycarbonate structure functionalized with boronic acid. Also, the acidity-sensitive covalent boronate ester bond can be formed between the boronic acid and one or more catechol moieties of the one or more chemical compounds. In one or more embodiments, the one or more chemical compounds can be one or more molecular cargos 402 described herein; including, but not limited to: AMP, a chemical compound comprising 1,2-diol, a combination thereof, and/or the like. Additionally, to facilitate the conjugation at 1302, the one or more chemical compounds and the one or more copolymers can be mixed at a molar ratio of chemical compound to copolymer ranging from greater than or equal to 1:1 and less than or equal to 5:1.

For example, the conjugating at 1302 can be performed in accordance with the first conjugation scheme 400 and/or the second conjugation scheme 600 described herein. For instance, the one or more copolymers can comprise the first polycarbonate structure 104 (e.g., functionalized with an arylboronic acid, such as phenylboronic acid). In various embodiments, the one or more copolymers can be the first polymercarrier 100 and/or the second polymer carrier 106, and/or can comprise a PEG structure as described herein. Further, the acidity-sensitive covalent boronate ester bond can be formed at a pH near the pKa of the boronic acid functional group. Moreover, the acidity-sensitive covalent boronate ester bond can be reversible in acidic environments (e.g., environments having a pH of less than 7.4). In one or more embodiments, the one or more copolymers can be the one or more second polymer carriers 106, wherein further functionalization of the polycarbonate block with an amino group (e.g., comprising a tertiary amine) can serve as an integrated catalyst and enable the conjugation at 1302 to be performed under neutral conditions.

FIG. 14 illustrates a flow diagram of an example, non-limiting method 1400 that can facilitate transporting one or more chemical compounds across the BBB in accordance with one or more embodiments described herein. Repetitive description of like elements employed in other embodiments described herein is omitted for sake of brevity.

At 1402, the method 1400 can comprise conjugating one or more chemical compound (e.g., one or more molecular cargos 402) to one or more copolymers (e.g., one or more first polymer carriers 100 and/or one or more second polymer carriers 106) via an acidity-sensitive (e.g., a pH-sensitive) covalent boronate ester bond. The one or more copolymers can comprise a polycarbonate structure functionalized with boronic acid. Also, the acidity-sensitive covalent boronate ester bond can be formed between the boronic acid and one or more catechol moieties of the one or more chemical compounds. In one or more embodiments, the one or more chemical compounds can be one or more molecular cargos 402 described herein; including, but not limited to: AMP, a chemical compound comprising 1,2-diol, a combination thereof, and/or the like. Additionally, to facilitate the conjugation at 1302, the one or more chemical compounds and the one or more copolymers can be mixed at a molar ratio of chemical compound to copolymer ranging from greater than or equal to 1:1 and less than or equal to 3:1.

At 1404, the method 1400 can comprise introducing a base organocatalyst to the one or more chemical compounds and/or the one or more copolymers to accelerate formation of the acidity-sensitive covalent boronate ester bond. For example, the conjugating at 1402 can be facilitated by the introduction of base at 1404 in accordance with the first conjugation scheme 400 described herein. For instance, the one or more copolymers can comprise the first polycarbonate structure 104 (e.g., functionalized with an arylboronic acid, such as phenylboronic acid). In various embodiments, the one or more copolymers can be the first polymer carrier 100, and/or can comprise a PEG structure as described herein. Further, the acidity-sensitive covalent boronate ester bond can be formed at a pH near the pKa of the boronic acid functional group. Moreover, the acidity-sensitive covalent boronate ester bond can be reversible in acidic environments (e.g., environments having a pH of less than 7.4).

In one or more embodiments, the base organocatalyst can lower the pKa value of the boronic acid functional group to accelerate the conjugation at 1402. Example base organocatalysts can include, but are not limited to: TEA, DMAP, DIEA, pyridine, a combination thereof, and/or the like. Additionally, the base organocatalyst can be introduced to the chemical compounds and/or the one or more copolymers at an exemplary molar ratio of base to boronic acid ranging from greater than or equal to 0.05:1 and less than or equal to 1:1 (e.g., 0.1:1).

Figure 15:
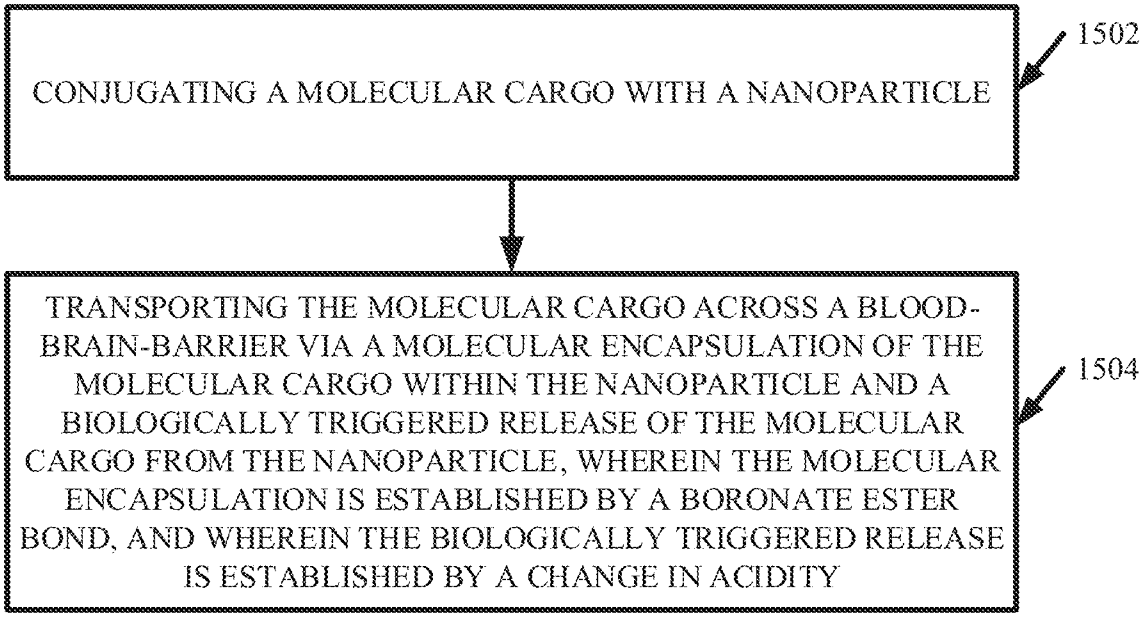
FIG. 15 illustrates a flow diagram of an example, non-limiting method that can facilitate transporting a molecular cargo across the BBB in accordance with one or more embodiments described herein.

FIG. 15 illustrates a flow diagram of an example, non-limiting method 1500 that can facilitate transporting one or more chemical compounds across the BBB in accordance with one or more embodiments described herein. Repetitive description of like elements employed in other embodiments described herein is omitted for sake of brevity.

At 1502, the method 1500 can comprise conjugating one or more molecular cargos 402 with one or more nanoparticles (e.g., one or more first polymer carriers 100 and/or one or more second polymer carriers 106). For example, the conjugating at 1502 can be performed in accordance with the first conjugation scheme 400 and/or the second conjugation scheme 600. In one or more embodiments, the one or more molecular cargos 402 can be one or more therapeutic chemical compounds comprising one or more catechol moieties. Additionally, the one or more nanoparticles can comprise one or more polycarbonate structures functionalized with boronic acid.

At 1504, the method 1500 can comprise transporting the molecular cargo 402 across the BBB via a molecular encapsulation of the one or more molecular cargos 402 within the one or more nanoparticles and/or a biologically triggered release of the one or more molecular cargos 402 from the one or more nanoparticles. The molecular encapsulation can be established by the conjugating at 1502 via a boronate ester bond between the boronic acid functional group of the one or more nanoparticles and the one or more catechol moieties of the one or more molecular cargos 402. Additionally, the biologically triggered release can be established by a change in acidity of the environment surround the one or more loaded nanoparticles.

For instance, the boronate ester bond can be formed in an environment having a pH vale near the pKa value of the boronic acid. Formation of the boronate ester bond can facilitate the molecular encapsulation of the one or more molecular cargos 402 into the one or more nanoparticles (e.g., the one or more first polymer carriers 100 and/or the one or more second polymer carriers 106) to establish one or more loaded nanoparticles (e.g., the one or more first loaded polymers 404 and/or the one or more second loaded polymers 602). Additionally, changing the acidity of the environment surrounding the loaded nanoparticles can trigger a reverse of the boronate ester bond; thereby, releasing the one or more molecular cargos 402 from the one or more nanoparticles. Further, the change in acidity can be caused by one or more biological responses to the one or more loaded nanoparticles crossing the BBB. For instance, upon crossing the BBB, the one or more loaded nanoparticles can experience a drop in pH below 7.4; thereby, catalyzing a reverse of the boronate ester bond and/or a release of the one or more molecular cargos 402.

FIG. 16 illustrates a flow diagram of an example, non-limiting method 1600 that can facilitate transporting one or more chemical compounds across the BBB in accordance with one or more embodiments described herein. Repetitive description of like elements employed in other embodiments described herein is omitted for sake of brevity.

At 1602, the method 1600 can comprise conjugating one or more molecular cargos 402 with one or more nanoparticles (e.g., one or more first polymer carriers 100 and/or one or more second polymer carriers 106). For example, the conjugating at 1502 can be performed in accordance with the first conjugation scheme 400 and/or the second conjugation scheme 600. In one or more embodiments, the one or more molecular cargos 402 can be one or more therapeutic chemical compounds comprising one or more catechol moieties. Additionally, the one or more nanoparticles can comprise one or more polycarbonate structures functionalized with boronic acid.

At 1604, the method 1600 can comprise transporting the molecular cargo 402 across the BBB via a molecular encapsulation of the one or more molecular cargos 402 within the one or more nanoparticles and/or a biologically triggered release of the one or more molecular cargos 402 from the one or more nanoparticles. The molecular encapsulation can be established by the conjugating at 1602 via a boronate ester bond between the boronic acid functional group of the one or more nanoparticles and the one or more catechol moieties of the one or more molecular cargos 402. Additionally, the biologically triggered release can be established by a change in acidity of the environment surround the one or more loaded nanoparticles.

For instance, the boronate ester bond can be formed in an environment having a pH vale near the pKa value of the boronic acid. Formation of the boronate ester bond can facilitate the molecular encapsulation of the one or more molecular cargos 402 into the one or more nanoparticles (e.g., the one or more first polymer carriers 100 and/or the one or more second polymer carriers 106) to establish one or more loaded nanoparticles (e.g., the one or more first loaded polymers 404 and/or the one or more second loaded polymers 602). Additionally, changing the acidity of the environment surrounding the loaded nanoparticles can trigger a reverse of the boronate ester bond; thereby, releasing the one or more molecular cargos 402 from the one or more nanoparticles. Further, the change in acidity can be caused by one or more biological responses to the one or more loaded nanoparticles crossing the BBB. For instance, upon crossing the BBB, the one or more loaded nanoparticles can experience a drop in pH below 7.4; thereby, catalyzing a reverse of the boronate ester bond and/or a release of the one or more molecular cargos 402.

At 1606, the method 1600 can further comprise inhibiting, by the molecular encapsulation, oxidation of the one or more molecular cargos 402. The molecular encapsulation established by the boronate ester bond can protect the one or more molecular cargos 402 from oxidation while the one or more loaded nanoparticles reach the BBB and/or experience uptake by the one or more brain cells. For example, the one or more one or more catechol moieties (e.g., and/or other hydroxyl groups comprised within the one or more molecular cargos 402) can render the one or more molecular cargos 402 susceptible to oxidation. In one or more instances, interaction of the one or more catechol moieties with the one or more boronic acid functional groups can inhibit oxidation of the one or more catechol moieties by the formation of ester bonds, which can be less susceptible to oxidation than hydroxyl groups.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

It is, of course, not possible to describe every conceivable combination of components, products and/or methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A chemical compound, comprising:

a copolymer having a molecular backbone comprising a polyethylene glycol structure, a first polycarbonate structure, and a second polycarbonate structure, wherein the first polycarbonate structure is functionalized with an anionic boronate ester group conjugated with apomorphine, wherein the anionic boronate ester group releases the apomorphine based on a biological trigger such that the anionic boronate ester group retains the apomorphine and inhibits oxidation of the apomorphine in a basic environment and releases the apomorphine in an acidic environment, wherein the second polycarbonate structure is covalently bonded to an amino functional group, and wherein the chemical compound is characterized by a chemical structure:

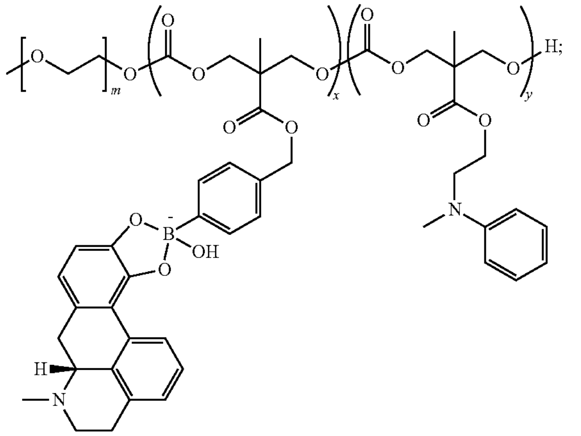

wherein "m" corresponds to a first integer greater than or equal to 45 and less than or equal to 454;

wherein "x" corresponds to a second integer greater than or equal to 2 and less than or equal to 50;

wherein "y" corresponds to a third integer greater than or equal to 2 and less than or equal to 50; and wherein about 75% of the copolymer is conjugated with the apomorphine.

2. The chemical compound of claim 1, wherein the chemical compound has a self-assembled particle size of less than or equal to 200 nanometers.

3. The chemical compound of claim 2, wherein the polyethylene glycol structure has a molecular weight of 10,000 daltons.

4. A chemical compound, comprising:

apomorphine bonded to a copolymer by an acidity-sensitive covalent anionic boronate ester bond, wherein the copolymer comprises a polycarbonate structure functionalized with boronic acid, wherein the acidity-sensitive covalent anionic boronate ester bond releases the apomorphine based on a biological trigger such that the acidity-sensitive covalent anionic boronate ester bond retains the apomorphine and inhibits oxidation of the apomorphine in a basic environment and releases the apomorphine in an acidic environment, wherein the acidity-sensitive covalent anionic boronate ester bond is formed between the boronic acid and a catechol moiety of the apomorphine, and wherein about 75% of the copolymer is conjugated with the apomorphine.

5. The chemical compound of claim 4, wherein the copolymer further comprises a second polycarbonate structure functionalized with an amino group.

6. The chemical compound of claim 4, wherein the chemical compound has a structure characterized by a formula:

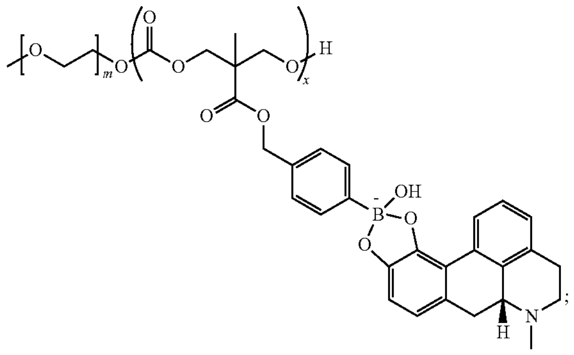

wherein "m" corresponds to a first integer greater than or equal to 45 and less than or equal to 454; and wherein "x" corresponds to second integer greater than or equal to 2 and less than or equal to 100.

7. The chemical compound of claim 1, wherein the basic environment has a pH value of 7.4, and wherein the acidic environment has a pH value of greater than or equal to 4.0 and less than or equal to 6.8.

8. The chemical compound of claim 1, wherein the conjugation amount of about 75% is achieved with a loading ratio of the apomorphine to the first polycarbonate structure at a 3:1 ratio for a reaction time of about 5 minutes.

9. The chemical compound of claim 4, wherein the basic environment has a pH value of 7.4, and wherein the acidic environment has a pH value of greater than or equal to 4.0 and less than or equal to 6.8.

10. The chemical compound of claim 4, wherein the conjugation amount of about 75% is achieved with a loading ratio of the apomorphine to the copolymer at a 3:1 ratio for a reaction time of about 5 minutes.

11. The chemical compound of claim 4, wherein the conjugation amount of about 75% is achieved by the presence of a basic organocatalyst.

12. The chemical compound of claim 4, wherein the conjugation amount of about 75% is achieved by the incorporation of one or more amine groups onto the polycarbonate structure.

13. The chemical compound of claim 4, wherein the chemical compound has a self-assembled particle size of less than or equal to 200 nanometers.

14. A chemical compound, comprising:

apomorphine bonded to a copolymer by an acidity-sensitive covalent anionic boronate ester bond, wherein the chemical compound has a structure characterized by a formula:

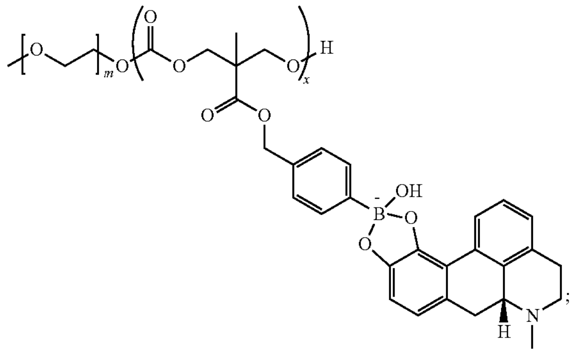

wherein "m" corresponds to a first integer greater than or equal to 45 and less than or equal to 454;

wherein "x" corresponds to second integer greater than or equal to 2 and less than or equal to 100; and wherein about 75% of the chemical compound is conjugated with the apomorphine.

15. The chemical compound of claim 14, wherein the acidity-sensitive covalent anionic boronate ester bond releases the apomorphine based on a biological trigger such that the acidity-sensitive covalent anionic boronate ester bond retains the apomorphine and inhibits oxidation of the apomorphine in a basic environment and releases the therapeutic compound in an acidic environment.

16. The chemical compound of claim 15, wherein the basic environment has a pH value of 7.4, and wherein the acidic environment has a pH value of greater than or equal to 4.0 and less than or equal to 6.8.

17. A chemical compound, comprising:

apomorphine bonded to a copolymer by an acidity-sensitive covalent anionic boronate ester bond, wherein the chemical compound has a structure characterized by a formula:

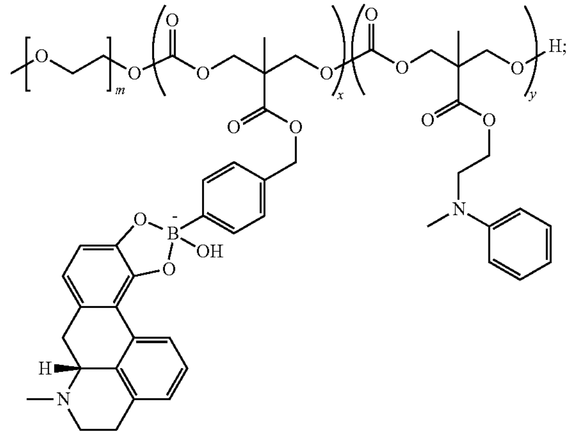

wherein "m" corresponds to a first integer greater than or equal to 45 and less than or equal to 454;

wherein "x" corresponds to a second integer greater than or equal to 2 and less than or equal to 50;

wherein "y" corresponds to a third integer greater than or equal to 2 and less than or equal to 50; and wherein about 75% of the chemical compound is conjugated with the apomorphine.

* * * * *